US010265413B2

(12) United States Patent
Ofner, III et al.

(10) Patent No.: US 10,265,413 B2
(45) Date of Patent: Apr. 23, 2019

(54) HIGH MOLECULAR WEIGHT BIODEGRADABLE GELATIN-DOXORUBICIN CONJUGATE

(71) Applicant: UNIVERSITY OF THE SCIENCES IN PHILADELPHIA, Pennsylvania, PA (US)

(72) Inventors: Clyde M. Ofner, III, Philadelphia, PA (US); Chris Cammarata, Philadelphia, PA (US); Brian Rhodes, Philadelphia, PA (US); Darren Wu, Philadelphia, PA (US)

(73) Assignee: UNIVERSITY OF THE SCIENCES IN PHILADELPHIA, Philadelphia, PA (US)

( * ) Notice: Subject to any disclaimer, the term of this patent is extended or adjusted under 35 U.S.C. 154(b) by 0 days.

(21) Appl. No.: 15/524,931

(22) PCT Filed: Oct. 30, 2015

(86) PCT No.: PCT/US2015/058265
§ 371 (c)(1),
(2) Date: May 5, 2017

(87) PCT Pub. No.: WO2016/077083
PCT Pub. Date: May 19, 2016

(65) Prior Publication Data
US 2017/0354741 A1 Dec. 14, 2017

Related U.S. Application Data

(60) Provisional application No. 62/075,481, filed on Nov. 5, 2014.

(51) Int. Cl.
*A61K 47/64* (2017.01)
*A61K 31/704* (2006.01)
*A61K 47/65* (2017.01)
*A61K 47/69* (2017.01)

(52) U.S. Cl.
CPC ........ *A61K 47/6435* (2017.08); *A61K 31/704* (2013.01); *A61K 47/64* (2017.08); *A61K 47/65* (2017.08); *A61K 47/6903* (2017.08)

(58) Field of Classification Search
None
See application file for complete search history.

(56) References Cited

U.S. PATENT DOCUMENTS

| | | | |
|---|---|---|---|
| 2,518,666 A * | 8/1950 | Damschroder | G03C 1/047 264/117 |
| 8,043,631 B2 | 10/2011 | Au | |
| 8,840,874 B2 | 9/2014 | Ayelet et al. | |
| 2002/0192289 A1 | 12/2002 | Zheng | |
| 2008/0248097 A1 | 10/2008 | Kwon et al. | |
| 2009/0181090 A1 | 7/2009 | Dreis | |
| 2010/0291021 A1 | 11/2010 | Vetter | |
| 2011/0053848 A1 | 3/2011 | Cleemann | |
| 2013/0045266 A1 | 2/2013 | Choi | |

FOREIGN PATENT DOCUMENTS

| | | |
|---|---|---|
| AU | 2013266987 B2 | 1/2014 |
| WO | 2007/134118 A2 | 11/2007 |

OTHER PUBLICATIONS

Das et al., "Sildenafil increases chemotherapeutic efficacy of doxorubicin in prostate cancer and ameliorates cardiac dysfunction", Proc Natl Acad Sci USA 107(42) 18202-18207 (2010).
Durand et al., "Flow cytometry studies of intracellular adriamycin in single cells in vitro", Cancer Res 41(9 Pt 1) 3489-3494 (1981).
Ghoroghchian et al., "Bioresorbable Vesicles Formed through Spontaneous Self-Assembly of Amphiphilic Poly (ethylene oxide)-block-polycaprolactone", Macromolecules 39(5) 1673-1675 (2006).
Goren et al., "Nuclear delivery of doxorubicin via folate-targeted liposomes with bypass of multidrug-resistance efflux pump", Clin Cancer Res 6(5) 1949-1957 (2000).
Li et al., "Polymer-drug conjugates: recent development in clinical oncology", Adv Drug Deliv Rev 60(8) 886-898 (2008).
Matsumura et al., "Phase I clinical trial and pharmacokinetic evaluation of NK911, a micelle-encapsulated doxorubicin", Br J Cancer 91(10) 1775-1781 (2004).
Minko et al."Efficacy of the chemotherapeutic action of HPMA copolymer-bound doxorubicin in a solid tumor model of ovarian carcinoma", Int J Cancer 86(1) 108-117 (2000).
Ranson et al., "Treatment of advanced breast cancer with sterically stabilized liposomal doxorubicin: results of a multicenter phase II trial", J Clin Oncol 15(10) 3185-3191 (1997).
Taylor et al., "Different mechanisms of decreased drug accumulation in doxorubicin and mitoxantrone resistant variants of the MCF7 human breast cancer cell line", Br J Cancer 63(6) 923-929 (1991).
Vasey et al., "Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee", Clin Cancer Res 5(1) 83-94 (1999).
Wang et al., "Pharmacokinetics and tissue distribution of PGG-paclitaxel, a novel macromolecular formulation of paclitaxel, in nu/nu mice bearing NCI-460 lung cancer xenografts", Cancer Chemother Pharmacol 65(3) 515-526 (2010).
Wu et al., "Adsorption and degradation of doxorubicin from aqueous solution in polypropylene containers", AAPS PharmSciTech 14(1) 74-77 (2013).
Wu et al., "Preparation, drug release, and cell growth inhibition of a gelatin: doxorubicin conjugate", Pharm Res 30(8) 2087-2096 (2013).
Zeng et al., "Modeling drug-carrier interaction in the drug release from nanocarriers", J Drug Deliv vol. 2011 (15 pages) (2011).
Zhang et al., "Tumor pH and its measurement", J Nucl Med 51(8) 1167-1170 (2010).
Lu, Dx et al., "Novel pH-Sensitive Drug Delivery System Based on Natural Polysaccharide for Doxorubicin Release", Chinese Journal of Polymer Science 26(3) 69-374 (2008).

\* cited by examiner

*Primary Examiner* — Eric Olson
(74) *Attorney, Agent, or Firm* — Nixon Peabody LLP

(57) ABSTRACT

Disclosed herein are high molecular weight compounds comprising gelatin and doxorubicin, where the gelatin is covalently linked to doxorubicin through a cleavable linker. The cleavable linker can be cleaved under appropriate physiological conditions, and thus lead to the freeing of doxorubicin. The free doxorubicin can then exert its cytotoxic effects on cancer cells. Disclosed herein are methods of making the high molecular weight gelatin-doxorubicin conjugates and methods of use of the same.

21 Claims, 6 Drawing Sheets

HIGH MOLECULAR WEIGHT BIODEGRADABLE GELATIN-DOXORUBICIN CONJUGATE

CROSS-REFERENCE TO RELATED APPLICATIONS

This application is a 35 U.S.C. § 371 National Stage Application of International Application No. PCT/US15/58265 filed Oct. 30, 2015, which designates the United States, and which claims the benefit under 35 U.S.C. § 119(e) of the U.S. Provisional Application No. 62/075,481, filed Nov. 5, 2014, the content of both of which are incorporated herein by reference in their entirety.

GOVERNMENT SUPPORT

This invention was made with government support under grant 1R15CA135421-01A1 awarded by the National Institutes of Health (NIH) and National Cancer Institute (NCI). The government has certain rights in the invention.

TECHNICAL FIELD

The present invention relates to compositions comprising biodegradable polymer-drug conjugates, and anti-cancer treatments.

BACKGROUND

A major challenge in cancer chemotherapy is the selective delivery of small molecule anti-cancer agents to cancer cells. Doxorubicin (DOX) is a potent antineoplastic agent that is effective against a wide range of solid tumors and lymphomas but it is also associated with an irreversible cardiomyopathy above cumulative doses of 550 mg/m$^2$ (Chabner B A, et al., Cytotoxic agents. In: Goodman and Gilman's the pharmacological basis of therapeutics. 12 ed. New York: McGraw-Hill, 2011). This and other toxic side effects make the drug a good candidate for localized drug delivery. DOX has been investigated in several macro-molecular delivery systems such as liposomes (Gabizon A, et al., Clin Pharmacokinet. 2003, 42, 419-36), synthetic copolymers of N-(2-hydroxypropyl)methacrylamide (HPMA) (Minko T, et al., Int J Cancer. 2000, 86, 108-17; Etrych T, et al., Macromol Biosci. 2002, 2, 43-52), other synthetic water soluble polymers (Duncan R, Vicent M J., Adv Drug Deliv. Rev. 2010, 62, 272-82), micelles (Matsumura Y, et al. Br J Cancer. 2004, 91, 1775-81; Kataoka K, et al. J Control Release Soc. 2000, 64, 143-53), polysaccharides (Lu D, et al., J Biomed Mater Res Part B: Appl Biomater. 2009, 89, 177-83) as well as block copolymer vesicles (or polymersomes) (Ghoroghchian P P, et al., Macromolecules. 2006, 39, 1673-5; Upadhyay K K, et al., Biomaterials. 2010, 31, 2882-92). Such delivery systems have demonstrated preferential accumulation in solid tumors compared to healthy tissue due to the enhanced permeation and retention effect (EPR) (Minko T, et al., Int J Cancer. 2000, 86, 108-17; Maeda H, J. Control Release Soc. 2000, 65, 271-84.). The resulting therapeutic advantages include an enhanced antitumor effect and reduced systemic toxicities (Minko T, et al., Int J Cancer. 2000, 86, 108-17; Duncan R., Nat Rev Drug Discov. 2003, 2, 347-60; Etrych T, et al., J Control Release Soc. 2008, 132, 184-92; Ayen W Y, Kumar N., Pharm Res. 2012, 29, 2522-33). Also, maximum tolerated doses of 5 to 10 fold greater than the free drug have been reported (Duncan R., Nat Rev Drug Discov. 2003, 2, 347-60; Sirova M, et al., Pharm Res. 2010, 27, 200-8). In addition, the ability to overcome drug resistance has been reported (Minko T, et al., J Control Release Soc. 1999, 59, 133-48; Nan A, et al., J Drug Target. 2005, 13, 189-97). These and similar delivery systems, however, have had concerns. An early HPMA-DOX conjugate showed little, if any, improved efficacy in Phase I clinical trials compared to the free drug (Vasey P A, et al. J Am Assoc Cancer Res. 1999, 5, 83-94). Mucocutaneous toxicities were reported from liposomal delivery of DOX (Ranson M R, et al., J Am Soc Clin Oncol. 1997, 15, 3185-91). And in a novel biodegradable delivery system not containing DOX, a polyglutamic acid carrier used with paclitaxol failed to demonstrate improved overall survival in Phase III clinical trials (Wang X, et al., Cancer Chemother Pharmacol. 2010, 65, 515-26).

Gelatin is the denatured and partially hydrolyzed product of collagen (Veis A. The macromolecular chemistry of gelatin. New York: Academic, 1964). It has been used as a macromolecular carrier to deliver several drugs including amphotericin B (Nahar M, et al., J Drug Target. 2010, 18, 93-105), methotrexate (Bowman B J, Ofner C M. Pharm Res. 2000, 17, 1309-15), and tumor necrosis factor (Tabata Y, et al., J Pharm Pharmacol. 1993, 45, 303-8). It has also been shown to have cell uptake (Ofner C M, et al., Int J Pharm. 2006, 308, 90-9). Its high molecular weight and biodegradability are attractive properties for use as a carrier in a DOX macromolecular delivery system. A sufficiently high molecular weight (e.g., 40 kDa or higher) can avoid glomerular filtration by the kidney leading to an extended circulation time and greater tumor accumulation by the EPR effect. Once the gelatin conjugate accumulates within the interstitial space of a tumor, its susceptibility to degradation by metalloproteinases, such as cathepsin B (Ofner C M, et al., Int J Pharm. 2006, 308, 90-9), would reduce the conjugate size and potentially enhance endocytotic uptake into the tumor cells. Recent reports describe encouraging results of high molecular weight HPMA-DOX conjugates containing cleavable links to allow breakdown in the body to lower molecular weight species (Etrych T, et al., J Control Release Soc. 2011, 154, 241-8; Etrych T, et al., J Control Release Soc. 2012, 164, 346-54). These lower sizes, however, are substantially larger than could occur with a biodegradable gelatin carrier.

Despite the interest in the art in synthesizing a high molecular weight gelatin-DOX conjugate, there are numerous synthetic challenges, particularly related to the degradation of high molecular weight gelatin during synthesis. For example, in an attempt to synthesize a high molecular weight gelatin-DOX conjugate (Wu et al., Pharm. Res. 2013, 20, 2087-2096), Wu et al. started with high molecular weight gelatin, but only produced low molecular weight gelatin-DOX conjugates (about 22 kDa). Accordingly, there is an unmet need in the art for high molecular weight gelatin-DOX conjugates and methods of production thereof.

SUMMARY

The invention is based, in part, on a novel synthesis methodology that can produce high molecular weight gelatin-DOX conjugates. Accordingly, in one aspect, the invention provides a high molecular weight compound comprising gelatin and DOX (i.e., a high molecular weight gelatin-DOX conjugate), where the gelatin is covalently linked to DOX through a cleavable linker.

In some embodiments, the compound has an average molecular weight of at least 40 kDa.

In some embodiments, the average molecular weight of the compound is in the range of 40 kDa to 600 kDa.

In some embodiments, the average molecular weight of the compound is about 150 kDa.

In some embodiments, the cleavable linker comprises a cleavable portion selected from a group consisting of: a pH-sensitive portion, a heat-sensitive portion, a light-sensitive portion, an enzymatically-cleavable portion, and a combination thereof.

In some embodiments, the pH-sensitive portion comprises a hydrazone bond, an ester, —S—S—, a carbamate, a vinyl ether, a silyl ether, or a combination thereof.

In some embodiments, the cleavable linker further comprises a spacer.

In some embodiments, the spacer is selected from a group consisting of: —O—, —S—, —NR$^a$—, —C(O)—, —SO—, —SO$_2$—, —C(O)NR$^a$—, —SO$_2$NR$^a$—, glycylglycine, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl; wherein backbone of the spacer can be interrupted or terminated by O, S, S(O), SO$_2$, N(R$^a$)$_2$, C(O), C(O)NR$^a$, substituted or unsubstituted aryl, substituted or unsubstituted heteroaryl, substituted or unsubstituted heterocyclic, and wherein R$^a$ is hydrogen, acyl, aliphatic or substituted aliphatic.

In some embodiments, the linker comprises a hydrazone bond and glycylglycine.

In some embodiments, the compound corresponds to Formula (I):

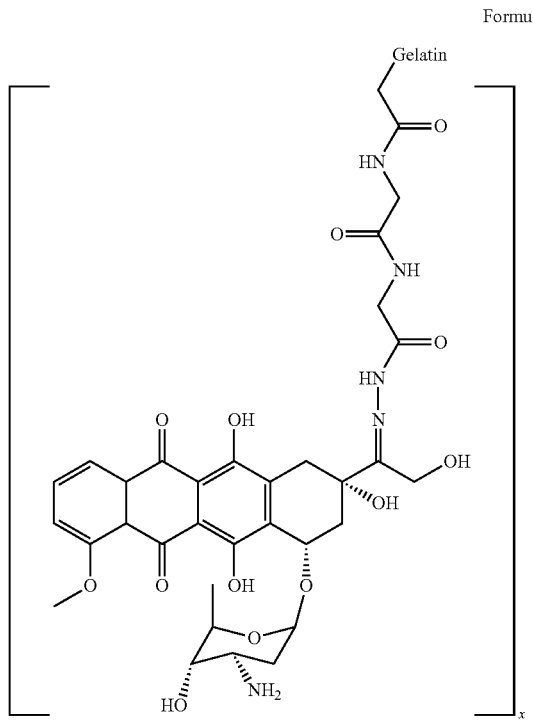

Formula I wherein x is determined by the molecular weight of the compound.

In some embodiments, the compound is biodegradable.

In some embodiments of the various aspects disclosed herein, the compound (e.g., the gelatin-DOX conjugate) described herein is stable in blood or serum. In other words, the conjugate is essentially or substantially resistant to enzymatic degradation in the blood or serum.

The inventors have discovered that reacting gelatin with doxorubicin in formamide surprisingly and unexpectedly results in high molecular weight gelatin-DOX conjugate without crosslinking. Accordingly, in one aspect, a method is provided herein for preparing the compounds described herein, the method comprising reacting a gelatin-linker conjugate with doxorubicin in formamide.

In some embodiments, the gelatin has an average molecular weight of at least 40 kDa.

In some embodiments, the average molecular weight of the gelatin is in the range of 40 kDa to 600 kDa.

In some embodiments, the average molecular weight of the gelatin is about 150 kDa.

In some embodiments, the method further comprises reacting gelatin dissolved in formamide with a linker to form the gelatin-linker conjugate; and precipitating the gelatin-linker conjugate with an alcohol.

In some embodiments, the alcohol is ethanol.

In some embodiments, the linker is cleavable.

In some embodiments, the linker comprises a cleavable portion selected from a group consisting of: a pH-sensitive portion, a heat-sensitive portion, a light-sensitive portion, an enzymatically-cleavable portion, and a combination thereof.

In some embodiments, the linker comprises a hydrazone bond.

In another aspect, a method is provided herein for preparing the compounds described herein, the method comprising reacting a gelatin-glycylglycine-hydrazide conjugate with doxorubicin in formamide.

In some embodiments, the gelatin has an average molecular weight of at least 40 kDa.

In some embodiments, the average molecular weight of the gelatin is in the range of 40 kDa to 600 kDa.

In some embodiments, the average molecular weight of the gelatin is about 150 kDa.

In some embodiments, the method further comprises: (i) reacting gelatin dissolved in formamide with glycylglycine to form a gelatin-glycylglycine conjugate; (ii) precipitating the gelatin-glycylglycine conjugate with a first alcohol; (iii) reacting the gelatin-glycylglycine conjugate with hydrazine in formamide to form a gelatin-glycylglycine-hydrazide conjugate; and (iv) precipitating the gelatin-glycylglycine-hydrazide conjugate with a second alcohol.

In some embodiments, the first alcohol is ethanol.

In some embodiments, the second alcohol is ethanol.

In some embodiments, the method further comprises adding 1-ethyl-3-(3-dimethylaminopropyl)carbodiimide (EDC) in step (i).

In some embodiments, the method further comprises adding EDC in step (iii).

In some embodiments, the glycylglycine is attached to a solid support in step (i).

In some embodiments, the solid support is a resin.

In some embodiments, the gelatin-glycylglycine-hydrazide conjugate is reacted with doxorubicin in pH less than 7 and in the presence of a drying agent.

In some embodiments, the method further comprises precipitating the compound comprising gelatin and doxorubicin with ethanol.

In yet another aspect, a method is provided herein for preparing the compounds described herein, the method comprising reacting an amino-blocked doxorubicin-hydrazide-glycylglycine conjugate with high molecular weight gelatin in formamide.

In some embodiments, the gelatin has an average molecular weight of at least 40 kDa.

In some embodiments, the average molecular weight of the gelatin is in the range of 40 kDa to 600 kDa.

In some embodiments, the average molecular weight of the gelatin is about 150 kDa.

In some embodiments, the method further comprises (i) reacting doxorubicin with an amine to form an amino-blocked doxorubicin; (ii) reacting the amino-blocked doxorubicin with hydrazine to form an amino-blocked doxorubicin-hydrazide conjugate; and (iii) reacting the amino-blocked doxorubicin-hydrazide conjugate with glycylglycine to form the amino-blocked doxorubicin-hydrazide-glycylglycine conjugate.

In a further aspect, a method is provided herein for treating cancer in a subject, the method comprising administering a pharmaceutically-effective amount of the compound described herein.

In some embodiments, the cancer is selected from a group consisting of Lymphoma, Leukemia, Sarcoma, Lung cancer, Multiple myeloma, Neuroblastoma, Testicular cancer, Mesothelioma, Thyroid cancer, Ovarian tumor, Pancreatic tumor, Breast tumor, Bladder Neoplasm, Tumor of uterus, Prostatic Neoplasms, Gastrointestinal tumor, and Liver tumor.

In some embodiments, the administering is local or systemic.

In some embodiments, the subject is a mammal.

In some embodiments, the subject is a human,

Another aspect of the invention relates to the use of the compound described herein for the preparation of a medicament for the treatment of cancer.

DETAILED DESCRIPTION

Figure 1:
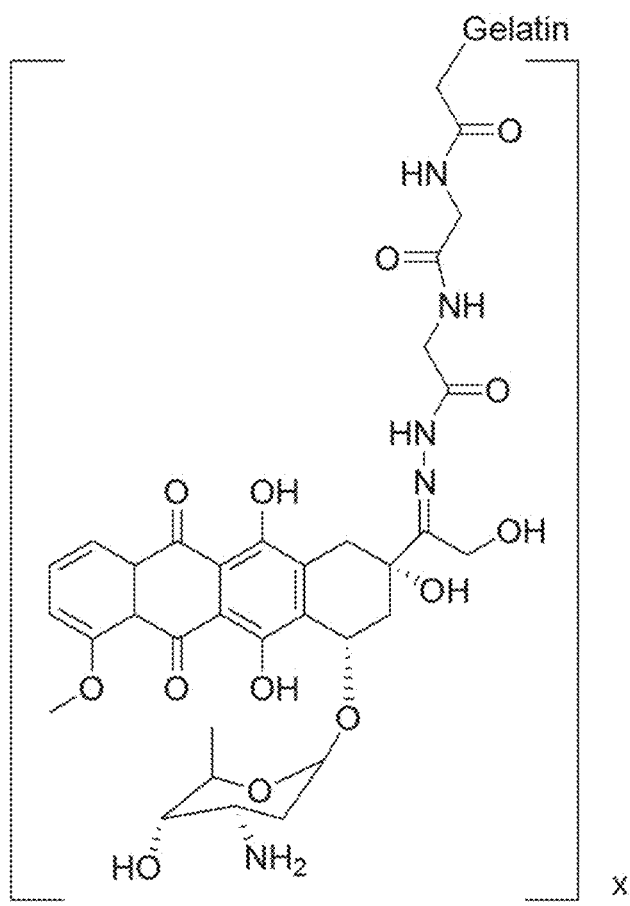
FIG. 1 shows the chemical structure of gelatin-DOX conjugates (GDox).

A novel synthesis scheme was devised that could prevent the degradation of high molecular weight gelatin during synthesis. As a result, the inventor has successfully produced a high molecular weight gelatin-DOX conjugate, wherein the gelatin is covalently linked to DOX through a cleavable linker. As used herein, the term "high molecular weight gelatin-DOX conjugate" refers to a gelatin-DOX conjugate having an average molecular weight of at least 40 kDa, at least 50 kDa, at least 60 kDa, at least 70 kDa, at least 80 kDa, at least 90 kDa, at least 100 kDa, at least 110 kDa, at least 120 kDa, at least 130 kDa, at least 140 kDa, at least 150 kDa, at least 160 kDa, at least 170 kDa, at least 180 kDa, at least 190 kDa, or at least 200 kDa. In some embodiments, the high molecular weight gelatin-DOX conjugate has a molecular weight of no more than 1000 kDa. In some embodiments, the high molecular weight gelatin-DOX conjugate has a molecular weight of no more than 750 kDa. The cleavable linker permits the dissociation of DOX from the conjugate when the conjugate reaches a desired site (e.g, cancer cells or the interstitial fluid of tumors). Embodiments of the invention thus relate to a high molecular weight compound comprising gelatin and DOX, methods of production of the same, and methods of use of the same.

Gelatin-DOX Compounds

In one aspect, the invention provides a high molecular weight compound comprising gelatin and DOX (i.e., a high molecular weight gelatin-DOX conjugate), where the gelatin is covalently linked to DOX through a cleavable linker. Without limitations, the molecular weight can be the peak average molecular weight (Mp), the number average molecular weight (Mn), or the weight average molecular weight (Mw).

A well-known biopolymer derived from collagen, gelatin is commercially available from vendors such as Sigma Aldrich, Kind and Knox. DOX is a well-known chemotherapeutic agent, and its IUPAC name is (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione.

In some embodiments, the compound has an average molecular weight of at least 40 kDa, at least 50 kDa, at least 60 kDa, at least 70 kDa, at least 80 kDa, at least 90 kDa, at least 100 kDa, at least 110 kDa, at least 120 kDa, at least 130 kDa, at least 140 kDa, at least 150 kDa, at least 160 kDa, at least 170 kDa, at least 180 kDa, at least 190 kDa, at least 200 kDa, at least 300 kDa, or at least 400 kDa. In some embodiments, the compound has an average molecular weight in the range of 40 kDa to 600 kDa, 40 kDa to 500 kDa, 40 kDa to 400 kDa, 40 kDa to 300 kDa, 40 kDa to 250 kDa, 40 kDa to 225 kDa, 40 kDa to 200 kDa, 40 kDa to 175 kDa, 40 kDa to 150 kDa, 40 kDa to 125 kDa, 40 kDa to 100 kDa, 60 kDa to 400 kDa, 60 kDa to 300 kDa, 60 kDa to 250 kDa, 60 kDa to 225 kDa, 60 kDa to 200 kDa, 60 kDa to 175 kDa, 60 kDa to 150 kDa, 60 kDa to 125 kDa, or 60 kDa to 100 kDa. In some embodiments, the compound has an average molecular weight of about 150 kDa.

The cleavable linker permits the dissociation of DOX from the compound under a particular stimulus. This can be very useful, for example, in drug delivery. A variety of stimuli are suitable for the invention which include, but are not limited to, light, temperature, pH, radiation, ultrasound, enzyme, and a combination thereof. In some embodiments, the cleavable linker comprises a cleavable portion. In some embodiments, the cleavable portion is selected from a group consisting of: a pH-sensitive portion, a heat-sensitive portion, a light-sensitive portion, an enzymatically-cleavable portion, and a combination thereof.

In some embodiments, the cleavable portion is pH-sensitive. The pH-sensitive portion can be stable under certain pH conditions, and then become unstable and thus cleavable when the pH is changed to other conditions. The change in pH can be, for example, from acidic to basic conditions, from basic to acidic conditions, from mildly acidic to strongly acidic conditions, or from mildly basic to strongly basic conditions. In some embodiments, the absolute value of the pH change can be at least 0.5, at least 1, at least 2, at least 3, at least 4, at least 5, at least 6, or at least 7. For example, the pH-sensitive portion is stable under typical physiological conditions where pH is around 7.4. When the pH is reduced to below a threshold level, for example, pH around 6, the pH-sensitive portion can be cleaved by hydrogen ions. In some embodiments, the pH-sensitive portion comprises a hydrazone bond, a cis-aconityl linkage, an ester, —S—S—, a carbamate, a vinyl ether, a silyl ether, a ketal, an acetal, an imine, a siloxane, a silazane, a maleamate, an amide bond, an activated carboxylic acid derivative, or a combination thereof. In some embodiments, the pH-sensitive portion comprises a hydrazone bond. As used herein, the term "hydrazone bond" refers to a moiety of the formula —C═N—N—.

It is known that the environment of the lysosome of the cancer cell or the interstitial fluid of cancer is acidic (Lee, E. S., et al., *Journal of Controlled Release* 2008, 132, 164-170; Zhang, X., et al., *Journal of Nuclear Medicine* 2010, 51, 1167-1170). Thus a pH-sensitive cleavable portion that is cleavable in an acidic environment permits the release of DOX from the gelatin-DOX conjugate inside or in close proximity to cancer cells, but not at neutral pH during the circulation inside the body.

In some embodiments, the cleavable portion is heat-sensitive. In these embodiments, a change in temperature can cleave the cleavable portion. The change in temperature can be from a temperature to a lower temperature or a higher temperature.

In some embodiments, the cleavable portion is light-sensitive. Depending on the particular chemical nature, the light-sensitive portion can be cleaved by photons of a particular wavelength, a number of wavelengths, or a wavelength range. Examples of light sensitive portions include, but are not limited to, nitrophenyl glycine esters, exo- and endo-2-benzonorborneyl chlorides and methane sulfonates, 3-amino-3(2-nitrophenyl) propionic acid, 6-nitroveratryloxycarbonyl, and 1-2-(nitrophenyl)-ethyl. In some embodiments of the cleavable portion being light-sensitive, visible light can cleave the light-sensitive portion. In some embodiments of the cleavable portion being light-sensitive, ultraviolet light can cleave the light-sensitive portion. In some embodiments of the cleavable portion being light-sensitive, near infrared light can cleave the light-sensitive portion. It is known in the art that near-infrared light can penetrate the skin deeper and has fewer side effects on tissues than visible light or ultraviolet light, and thus near-infrared light is preferred in some drug delivery applications.

In some embodiments, the cleavable portion is cleavable by an enzyme. Examples of enzymatically cleavable portions include, but are not limited to, protease-sensitive amides or esters, beta-lactamase-sensitive beta-lactam analogs and linkers that are nuclease-cleavable, or glycosidase-cleavable.

In some embodiments, the cleavable linker further comprises a spacer. The spacer allows the adjustment of the spatial relationship (e.g., distance) between gelatin and DOX. In some embodiments, the spacer is covalently linked to the cleavable portion. In some embodiments, the spacer can comprise about 50 atoms or less, about 40 atoms or less, about 30 atoms or less, about 20 atoms or less, or about 10 atoms or less. In some embodiments, the spacer is selected from a group consisting of: —O—, —S—, —NR$^a$—, —C(O)—, —SO—, —SO$_2$—, —C(O)NR$^a$—, —SO$_2$NR$^a$—, glycylglycine, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl; wherein backbone of the spacer can be interrupted or terminated by O, S, S(O), SO$_2$, N(R$^a$)$_2$, C(O), C(O)NR$^a$, substituted or unsubstituted aryl, substituted or unsubstituted heteroaryl, substituted or unsubstituted heterocyclic, and wherein R$^a$ is hydrogen, acyl, aliphatic or substituted aliphatic.

In some embodiments, the spacer is covalently linked to gelatin, while the cleavable portion is covalently linked to DOX. In alternative embodiments, the spacer is covalently linked to DOX, while the cleavable portion is covalently linked to gelatin.

In some embodiments, more than one spacer is used, e.g., 2, 3, 4, 5, 6, or more.

In some embodiments, the cleavable linker comprises a hydrazone bond and glycylglycine.

In one embodiment, the hydrazone bond is covalently linked to gelatin, while glycylglycine is covalently linked to DOX. In another embodiment, the hydrazone bond is covalently linked to DOX, while glycylglycine is covalently linked to gelatin.

In some embodiments of the various aspects disclosed herein, the compound (e.g., the gelatin-DOX conjugate) described herein is stable in blood or serum. By stable in blood or serum is meant that less than 10% (e.g., 7.5%, 5%, 2.5%, 1%, 0.5% or less) of the conjugates is degraded when incubated in blood or serum for at least 12 (e.g., 12, 16, 20, 24, 28, 32, 36 or more) hours at room temperature. Stability in blood or serum can be determined using the protocol detailed in the Examples section, e.g., Example 4.

In some embodiments, the compound corresponds to Formula (I):

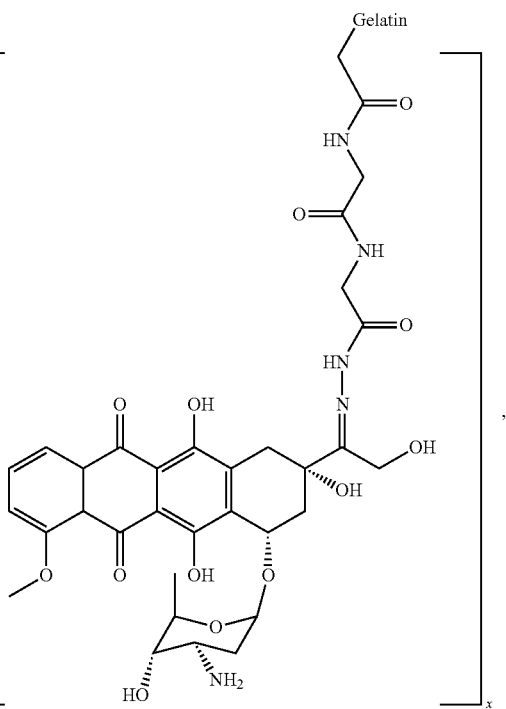

Formula I in which x is determined by the molecular weight of the compound.

The molecular weight of the compound described herein can be determined by any known methods in the art, including, e.g., but not limited to, SDS-PAGE gel, size exclusion chromatography (SEC), mass spectroscopy, or any combinations thereof. In some embodiments, the molecular weight of the compound can be determined by SEC. SEC can be used as a measure of both the molecular weight and the polydispersity of a polymer, that is, the ability to be able to find the molecular weight distribution of polymer molecules. In SEC, standards such as polystyrene sulfonate can be used to determine the molecular weights. The molecular weight distribution of the fragments present in the high molecular weight gelatin-DOX compositions can be quantified using any art-recognized methods.

The high molecular weight gelatin-DOX compositions described herein can have a broad molecular weight distribution or a narrow molecular weight distribution. One measure of molecular weight distribution is the polydispersity index, or the ratio of Mw/Mn, where Mw is weight-average molecular weight and Mn is number-average molecular weight. In general, the smaller the polydispersity index, the narrower the molecular weight distribution is. In some embodiments, the polydispersity index is at least 1, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, at least 3.0, at least 3.5, at least 4, at least 4.5, or at least 5. For a high molecular weight gelatin-DOX composition having a broad molecular weight distribution, methods such as chromatography can be utilized to isolate desired molecular weight segments.

The high molecular weight gelatin-DOX compositions described herein can exhibit a continuous or discrete molecular weight distribution. As used herein, the term "continuous molecular weight distribution" refers to a distribution of molecular weight having any sub-ranges between a specified range. As used herein, the term "discrete molecular weight distribution" refers to a distribution of molecular weight having only certain sub-ranges between the specified range.

In some embodiments, the compounds of the present invention are biodegradable. Gelatin is known as a biodegradable polymer and has been evaluated as a carrier material for applications such as drug delivery. The biodegradability of gelatin has been disclosed, for example, in Patel et al., Acta Biomater. 2008, 4, 1126-1138 and U.S. Pat. No. 5,639,620. The degrading rate of the compounds of the present invention can depend on factors including, but not limited to, molecular weight of the compound and physiological conditions.

Methods of Making

Figures 2A, 2B, 2C:
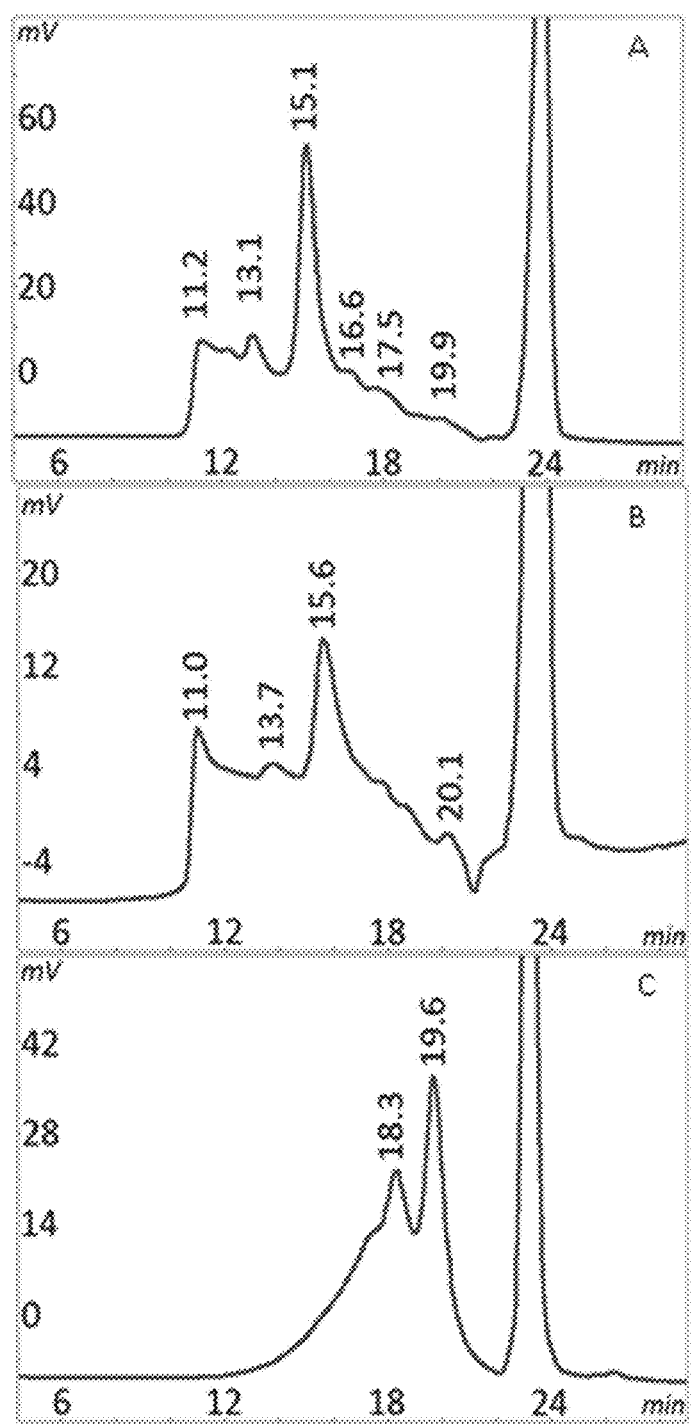
FIGS. 2A-2C are plots of size exclusion chromatograms of starting gelatin (FIG. 2A), GDox (FIG. 2B), and a low molecular weight GDox (FIG. 2C) previously reported (Wu, D. C., et al., *Pharm Res* 2013, 30, 2087-2096). Peaks at around 11 minutes corresponds to molecular weights >310 kDa, around 13 minutes corresponds to molecular weight of 200 kDa, 15 minutes to 100 kDa, 18 minutes to 26 kDa and 20 minutes to 16 kDa.

Synthesis of a gelatin-DOX conjugate (GDox) and its degradation were previously reported (Wu, D. C., et al., *Pharm Res* 2013, 30, 2087-2096). Synthesis was conducted under aqueous conditions beginning with gelatin of a molecular weight of 159 kDa with blocked amino groups followed by additional steps using the carbodiimide, EDC, and separation steps using size exclusion chromatography resulting in a low molecular weight GDox of approximately 22 kDa. The inventors have discovered that conducting the chemical reaction in formamide surprisingly and unexpectedly results in high molecular weight GDox. As disclosed herein, changing the reaction solvent to formamide and conducting EDC coupling reactions at an acid pH while also using ethanol precipitation for separation steps instead of size exclusion chromatography resulted in a high molecular weight GDox. FIG. 2B demonstrates the production of high molecular weight GDox that was absent in the results of Wu et al. (FIG. 2C).

Accordingly, provided herein are novel methodologies for preparing the compounds of the invention. Specific methodologies are described in more detail below and in the Examples section. In general, a synthesis methodology can start with high molecular weight gelatin, attach the cleavable linker to gelatin via one or more chemical reactions, and then further attach DOX to the cleavable linker that is attached to the gelatin. Another synthesis methodology can start with DOX, attach the cleavable linker to DOX via one or more chemical reactions, and then further attach high molecular weight gelatin to the cleavable linker that is attached to DOX. The gelatin and/or DOX can be chemically blocked during the synthesis but this is not necessary.

Gelatin comprises carboxyl groups which can be used as sites for attachment (e.g., attaching the cleavable linker). Methods for activating carboxyl groups for chemical synthesis are well known in the art. For example, 1-ethyl-3-[3-dimethylaminopropyl]carbodiimide hydrochloride (EDC) is a reagent capable of activating carboxyl groups in an acid solvent. Reaction conditions should be such that high molecular weight gelatin does not get substantially degraded during the synthesis.

As for DOX, the coupling of DOX to carriers has been studied in numerous reports (see, e.g., Etrych et al., J. Control Release Soc. 2011, 154, 241-248; Etrych et al., J. Control Release Soc. 2012, 164, 346-354). In one aspect, a method is provided herein for preparing the compounds described herein, the method comprising reacting gelatin or a gelatin-linker conjugate with doxorubicin in formamide. In some embodiments, the method further comprises reacting gelatin dissolved in formamide with a linker to form the gelatin-linker conjugate. In some embodiments, alcohol such as ethanol can be used to precipitate reaction intermediates or the final product. For example, the reaction intermediate is a gelatin-linker conjugate or a precursor of the gelatin-linker conjugate.

Another aspect of the invention relates to a method of preparing the compounds described herein, the method comprising reacting a gelatin-glycylglycine-hydrazide conjugate with doxorubicin in formamide. In some embodiments, the method further comprises reacting gelatin dissolved in formamide with glycylglycine to form a gelatin-glycylglycine conjugate. The gelatin-glycylglycine conjugate can be precipitated with a solvent such as an alcohol. The gelatin-glycylglycine conjugate can react with hydrazine in formamide to form a gelatin-glycylglycine-hydrazide conjugate. The gelatin-glycylglycine-hydrazide conjugate can be precipitated with a solvent such as an alcohol. In some embodiments, the method further comprises adding 1-ethyl-3-(3-dimethylaminopropyl) carbodiimide (EDC) in the reaction between gelatin and glycylglycine. In some embodiments, the method further comprises adding EDC to facilitate the formation of the gelatin-glycylglycine-hydrazide conjugate. In some embodiments, the method further comprises, prior to the addition of doxorubicin hydrochloride, adding acid (e.g., acetic acid) to the reaction solution which comprise the gelatin-glycylglycine-hydrazide conjugate to increase the acidity of the solution. In some embodiments, the method further comprises adding a water drying agent (e.g., sodium sulfate) to facilitate the coupling between the gelatin-glycylglycinehydrazide conjugate and DOX. The compound comprising gelatin and DOX can be precipitated with an alcohol such as ethanol.

The compounds described herein can also be synthesized using a method comprising reacting an amino-blocked doxorubicin-hydrazide-glycylglycine conjugate with high molecular weight gelatin in formamide. In some embodiments, the method further comprises: (i) reacting doxorubicin with an amine to form an amino-blocked doxorubicin; (ii) reacting the amino-blocked doxorubicin with hydrazine to form an amino-blocked doxorubicin-hydrazide conjugate; (iii) reacting the amino-blocked doxorubicin-hydrazide conjugate with glycylglycine to form the amino-blocked doxorubicin-hydrazide-glycylglycine conjugate. In some embodiments, the amine 9-Fluorenylmethyl N-succinimidyl carbonate (i.e., Fmoc-OSu).

Solid phase peptide synthesis can also be utilized for the preparation of the compounds described herein. Some or all steps of the synthesis described herein can be done in the solid phase. For example, the reaction between gelatin and glycylglycine can occur while glycylglycine is attached to a solid support. The gelatin-glycylglycine conjugate can then be detached from the solid support.

Detailed description of solid phase peptide synthesis can be found, for example, in Peptides: Chemistry and Biology, N. Sewald, H.-D. Jakubke, Wiley-VCH Verlag GmbH, Weinheim, 2002 and Fmoc-Solid Phase Peptide Synthesis-A practical approach, W. C. Chan, P. D. White, Oxford University Press Inc. New York, 2000. Any type of support suitable in the practice of solid phase peptide synthesis can be used. In preferred embodiments, the support comprises a resin that can be made from one or more polymers, copolymers or combinations of polymers such as polyamide, polysulfamide, substituted polyethylenes, polyethyleneglycol, phenolic resins, polysaccharides, or polystyrene. The polymer support can also be any solid that is sufficiently insoluble and inert to solvents used in peptide synthesis. The solid support typically includes a linking moiety to which the growing peptide is coupled during synthesis and which can be cleaved under desired conditions to release the peptide from the support. Suitable solid supports can have linkers that are photo-cleavable, TFA-cleavable, HF-cleavable, fluoride ion-cleavable, reductively-cleavable; Pd(O)-cleavable; nucleophilically-cleavable; or radically-cleavable. Preferred linking moieties are cleavable under conditions such that the side-chain groups of the cleaved peptide are still substantially globally protected.

Examples of resins include trityl chloride resin, 4-methyltrityl chloride resin, 4-methoxytrityl chloride resin, 4-aminobutan-1-ol 2-chlorotrityl resin, 4-aminomethylbenzoyl 2-chlorotrityl resin, 3-aminopropan-1-ol 2-chlorotrityl resin, bromoacetic acid 2-chlorotrityl resin, cyanoacetic acid 2-chlorotrityl resin, 4-cyanobenzoic acid 2-chlorotrityl resin, glicinol 2-chlorotrityl resin, propionic 2-chlorotrityl resin, ethyleneglycol 2-chlorotrityl resin, N-Fmoc hydroxylamine 2-chlorotrityl resin, hydrazine 2-chlorotrityl resin. Some solid supports include polystyrene, which can be copolymerized with divinylbenzene, to form support material to which the reactive groups are anchored.

Other resins that are used in solid phase synthesis include "Wang" resins, which comprise a copolymer of styrene and divinylbenzene with 4-hydroxymethylphenyloxymethyl anchoring groups (Wang, S. S. 1973, J. Am. Chem. Soc.), and 4-hydroxymethyl-3-methoxyphenoxybutyric acid resin (Richter et al. (1994), Tetrahedron Letters 35(27):4705-4706). The Wang, 2-chlorotrityl chloride, and 4-hydroxymethyl-3-methoxyphenoxy butyric acid resins can be purchased from, for example, Calbiochem-Novabiochem Corp., San Diego, Calif.

In some embodiments of the methods of preparing the compounds described herein, the alcohol can be methanol, ethanol, propanol, or any combinations thereof.

In some embodiments of the methods of preparing the compounds described herein, the gelatin has an average molecular weight of at least 40 kDa, at least 50 kDa, at least 60 kDa, at least 70 kDa, at least 80 kDa, at least 90 kDa, at least 100 kDa, at least 110 kDa, at least 120 kDa, at least 130 kDa, at least 140 kDa, at least 150 kDa, at least 160 kDa, at least 170 kDa, at least 180 kDa, at least 190 kDa, or at least 200 kDa, at least 300 kDa, or at least 400 kDa. In some embodiments, the gelatin has an average molecular weight in the range of 40 kDa to 600 kDa, 40 kDa to 500 kDa, 40 kDa to 400 kDa, 40 kDa to 300 kDa, 40 kDa to 250 kDa, 40 kDa to 225 kDa, 40 kDa to 200 kDa, 40 kDa to 175 kDa, 40 kDa to 150 kDa, 40 kDa to 125 kDa, 40 kDa to 100 kDa, 60 kDa to 400 kDa, 60 kDa to 300 kDa, 60 kDa to 250 kDa, 60 kDa to 225 kDa, 60 kDa to 200 kDa, 60 kDa to 175 kDa, 60 kDa to 150 kDa, 60 kDa to 125 kDa, or 60 kDa to 100 kDa. In some embodiments, the gelatin has an average molecular weight of about 150 kDa. The gelatin can have any kind of molecular weight distribution (e.g., narrow or broad).

Pharmaceutical Compositions

In one aspect, the invention provides a pharmaceutical composition comprising the high molecular weight compound described herein. In some embodiments, the pharmaceutical composition comprises a pharmaceutically-acceptable carrier and/or diluent. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutical compositions of the present invention can be specially formulated for administration in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally the compounds described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Treatment

In yet another aspect, the invention provides a method of treating cancer in a subject, the method comprising administering a therapeutically-effective amount of the compound of the present invention. The method described herein can treat any cancer treatable by doxorubicin, for example, leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angio sarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma;

pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma.

Additional types of cancer include neoblastoma, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). The tumor may be a solid tumor or a non-solid tumor and may be a primary tumor or a disseminated metastatic (secondary) tumor.

The compounds disclosed herein or pharmaceutical compositions comprising the compounds thereof may be administered in any dose or dosing regimen. With respect to the therapeutic methods of the invention, it is not intended that the administration be limited to a particular mode of administration, dosage, or frequency of dosing.

The compounds of the present invention can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. In some embodiments, the route of administration is intravenous, e.g., intravenous injection. In some embodiments, the route of administration is rectal suppository administration. In some embodiments, the route of administration is oral inhalation.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection. In some embodiments, the compound is administered directly into the central nervous system.

In one embodiment, it may be desirable to administer the pharmaceutical compositions comprising the compounds disclosed herein locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes. In some embodiments, for certain solid tumors accessible by injection, an injection into the tumor site or its vicinity can be desirable.

In some embodiments, the pharmaceutical composition can be administered to a subject orally (e.g., in capsules, suspensions or tablets) or by parenteral administration. Conventional methods for oral administration include any one of the following; tablets, suspensions, solutions, emulsions, capsules, powders, syrups and the like are usable. Parenteral administration can include, for example, intramuscular, intravenous, intraarticular, intraarterial, intrathecal, subcutaneous, or intraperitoneal administration. The pharmaceutical composition can also be administered orally, transdermally, topically, by inhalation (e.g., intrabronchial, intranasal, oral inhalation or intranasal drops) or rectally. Administration can be local or systemic as indicated.

When administering the pharmaceutical composition parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils. The term "Dosage unit" form as used herein refers to physically discrete units suited as unitary dosages for the subjects to be treated; each unit containing a predetermined quantity of active compound calculated to produce the desired therapeutic effect in association with the required pharmaceutical carrier.

An effective amount, e.g., a therapeutically effective dose of the compound disclosed herein may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising the compound disclosed herein can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

The dosage can be determined by one of skill in the art and can also be adjusted by the individual physician in the event of any complication. Typically, the dosage of a composition comprising the compound disclosed herein can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

In some embodiments, the dosage of a composition comprising the compound disclosed herein can be administered in a dose of from about 20 mg/m² to about 5,000 mg/m² body surface area. For example, the dose can be from about 20 mg/m² to about 200 mg/m² body surface area; the dose can be from about 150 mg/m² to about 500 mg/m² body surface area; the dose can be from about 400 mg/m² to about 1000 mg/m² body surface area; the dose can be from about 900 mg/m² to about 5,000 mg/m² body surface area; the dose can be from about 200 mg/m² to about 1,000 mg/m² body surface area; or the dose can be from about 500 mg/m² to about 600 mg/m² body surface area.

The current standard dosage of DOX can also serve as a guideline for the dosage used in the method described herein. Current standard dosages for DOX are readily available information. Without wishing to be bound by theory, because the molecular design of the high molecular weight gelatin-DOX compounds can lead to drug localization within cancer cells, compounds described herein can permit enhanced efficacy and substantially reduced systemic drug toxicities A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the composition being administered, and the condition of the patient, the particular cancer to be treated, as well as the body weight or body surface area. The size of the dose is also determined by the existence, nature, and extent of any adverse side-effects that accompany the administration of a particular formulation, or the like in a particular subject. Therapeutic compositions are optionally tested in one or more appropriate in vitro and/or in vivo animal models of disease, and known to persons of ordinary skill in the art, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the pharmaceutical composition at various concentrations, e.g., as applied to the mass and overall health of the patient.

Embodiments of the various aspects disclosed herein can be described by one or more of the numbered paragraphs:

1. A high molecular weight compound comprising gelatin and doxorubicin, wherein the gelatin is covalently linked to doxorubicin through a cleavable linker.
2. The compound of paragraph 1, wherein the compound has an average molecular weight of at least 40 kDa.
3. The compound of paragraph 2, wherein the average molecular weight is in the range of 40 kDa to 600 kDa.
4. The compound of paragraph 3, wherein the average molecular weight is about 150 kDa.
5. The compound of any of paragraphs 1-4, wherein the cleavable linker comprises a cleavable portion selected from a group consisting of: a pH-sensitive portion, a heat-sensitive portion, a light-sensitive portion, an enzymatically-cleavable portion, and a combination thereof.
6. The compound of paragraph 5, wherein the pH-sensitive portion comprises a hydrazone bond, an ester, —S—S—, a carbamate, a vinyl ether, a silyl ether, or a combination thereof.
7. The compound of any of paragraphs 1-6, wherein the cleavable linker further comprises a spacer.
8. The compound of paragraph 7, wherein the spacer is selected from a group consisting of: —O—, —S—, —NR$^a$—, —C(O)—, —SO—, —SO$_2$—, —C(O)NR$^a$—, —SO$_2$NR$^a$—, glycylglycine, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherероaryl; wherein backbone of the spacer can be interrupted or terminated by O, S, S(O), SO$_2$, N(R$^a$)$_2$, C(O), C(O)NR$^a$, substituted or unsubstituted aryl, substituted or unsubstituted heteroaryl, substituted or unsubstituted heterocyclic, and wherein R$^a$ is hydrogen, acyl, aliphatic or substituted aliphatic.
9. The compound of any of paragraphs 1-4, wherein the linker comprises a hydrazone bond and glycylglycine.
10. The compound of any of paragraphs 1-4, corresponding to Formula (I):

Formula I

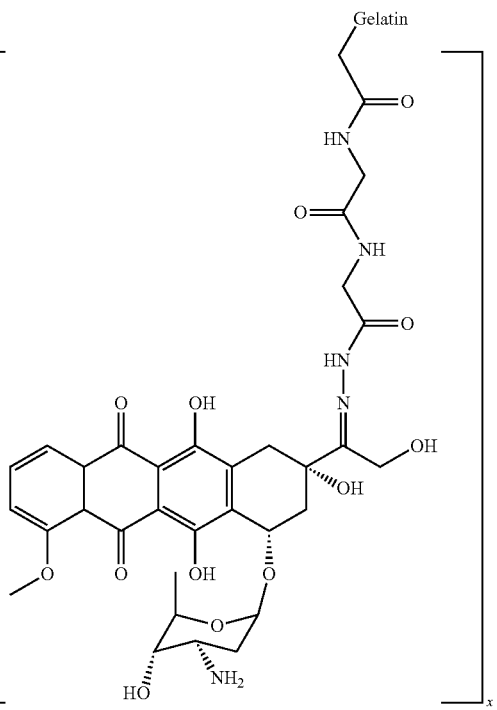

wherein x is determined by the molecular weight of the compound.

11. The compound of any of paragraphs 1-10, wherein the compound is biodegradable.
12. A method of preparing a compound comprising gelatin and doxorubicin, the method comprising reacting a gelatin-linker conjugate with doxorubicin in formamide.
13. The method of paragraph 12, wherein the gelatin has an average molecular weight of at least 40 kDa.
14. The method of paragraph 13, wherein the average molecular weight is in the range of 40 kDa to 600 kDa.
15. The method of paragraph 14, the average molecular weight is about 150 kDa.
16. The method of any of paragraphs 12-15, further comprising:
    (i) reacting gelatin dissolved in formamide with a linker to form the gelatin-linker conjugate; and
    (ii) precipitating the gelatin-linker conjugate with an alcohol.
17. The method of paragraph 16, wherein the alcohol is ethanol.
18. The method of paragraph 16 or 17, wherein the linker is cleavable.
19. The method of paragraph 18, wherein the linker comprises a cleavable portion selected from a group consisting of: a pH-sensitive portion, a heat-sensitive portion, a light-sensitive portion, an enzymatically-cleavable portion, and a combination thereof.
20. The method of paragraph 19, wherein the linker comprises a hydrazone bond.
21. A method of preparing a compound comprising gelatin and doxorubicin, the method comprising reacting a gelatin-glycylglycine-hydrazide conjugate with doxorubicin in formamide.
22. The method of paragraph 21, wherein the gelatin has an average molecular weight of at least 40 kDa.
23. The method of paragraph 22, wherein the average molecular weight is in the range of 40 kDa to 600 kDa.
24. The method of paragraph 23, the average molecular weight is about 150 kDa.
25. The method of any of paragraphs 21-24, further comprising:
    (i) reacting gelatin dissolved in formamide with glycylglycine to form a gelatin-glycylglycine conjugate;
    (ii) precipitating the gelatin-glycylglycine conjugate with a first alcohol;
    (iii) reacting the gelatin-glycylglycine conjugate with hydrazine in formamide to form the gelatin-glycylglycine-hydrazide conjugate; and
    (iv) precipitating the gelatin-glycylglycine-hydrazide conjugate with a second alcohol;
26. The method of paragraph 25, wherein the first alcohol is ethanol.
27. The method of paragraph 25 or 26, wherein the second alcohol is ethanol.
28. The method of any of paragraphs 25-27, further comprising adding 1-ethyl-3-(3-dimethylaminopropyl) carbodiimide (EDC) in step (i).
29. The method of any of paragraphs 25-28, further comprising adding EDC in step (iii).
30. The method of any of paragraphs 25-29, wherein glycylglycine is attached to a solid support in step (i).
31. The method of paragraph 30, wherein the solid support is a resin.
32. The method of any of paragraphs 21-31, wherein the gelatin-glycylglycine-hydrazide conjugate is reacted with doxorubicin in pH less than 7 and in the presence of a drying agent.
33. The method of any of paragraphs 21-32, further comprising precipitating the compound comprising gelatin and doxorubicin with ethanol.
34. A method of preparing a compound comprising gelatin and doxorubicin, the method comprising reacting an amino-blocked doxorubicin-hydrazide-glycylglycine conjugate with high molecular weight gelatin in formamide.
35. The method of paragraph 32 or 33, wherein the gelatin has an average molecular weight of at least 40 kDa.
36. The method of paragraph 35, wherein the average molecular weight is in the range of 40 kDa to 600 kDa.
37. The method of paragraph 36, the average molecular weight is about 150 kDa.
38. The method of any of paragraphs 34-37, further comprising:
    (i) reacting doxorubicin with an amine to form an amino-blocked doxorubicin;
    (ii) reacting the amino-blocked doxorubicin with hydrazine to form an amino-blocked doxorubicin-hydrazide conjugate; and
    (iii) reacting the amino-blocked doxorubicin-hydrazide conjugate with glycylglycine to form the amino-blocked doxorubicin-hydrazide-glycylglycine conjugate.
39. A method of treating cancer in a subject, the method comprising administering a pharmaceutically-effective amount of a compound of any of paragraphs 1-11 to the subject.
40. The method of paragraph 39, wherein the cancer is selected from a group consisted of
Lymphoma, Leukemia, Sarcoma, Lung cancer, Multiple myeloma, Neuroblastoma, Testicular cancer, Mesothelioma, Thyroid cancer, Ovarian tumor, Pancreatic tumor, Breast tumor, Bladder Neoplasm, Tumor of uterus, Prostatic Neoplasms, Gastrointestinal tumor, and Liver tumor.
    41. The method of paragraph 39 or 40, wherein the administering is local or systemic.
    42. The method of any of paragraphs 39-41, wherein the subject is a mammal.
    43. The method of paragraph 42, wherein the subject is a human.
    44. The use of a compound of any of paragraphs 1-11 for the preparation of a medicament for the treatment of cancer.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although any known methods, devices, and materials may be used in the practice or testing of the invention, the methods, devices, and materials in this regard are described herein.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein, the term "conjugate", when used as a noun, refers to a compound as a result of two or more molecules joined together to form one physical entity. For example, a gelatin-DOX conjugate means a compound as a result of gelatin and doxorubicin joined together. The molecules may attach together by linkers, chemical modification, peptide linkers, chemical linkers, covalent or non-covalent bonds, or protein fusion or by any means known to one skilled in the art. The joining may be permanent or reversible. In some embodiments, several linkers may be included in order to take advantage of desired properties of each linker and each molecule in the conjugate.

As used herein, the term "cleavable linker" is defined as a spacer molecule characterized by having a portion (e.g., a bond or multiple bonds) that can be cleaved by a cleaving agent that includes, but is not limited to, heat, light, pH, and enzyme.

As used herein, the term "biodegradable" describes a material which can decompose partially or fully under physiological conditions into breakdown products. The material under physiological conditions can undergo reactions or interactions such as hydrolysis (decomposition via hydrolytic cleavage), enzymatic catalysis (enzymatic degradation), and mechanical interactions. As used herein, the term "biodegradable" also encompasses the term "bioresorbable", which describes a substance that decomposes under physiological conditions to break down to products that undergo bioresorption into the host-organism, namely, become metabolites of the biochemical systems of the host organism. For example, a material is biodegradable if at least 10%, at least 20%, at least 30%, at least 40%, or more preferably, at least 50%, at least 60%, at least 70%, at least 80%, at least 90% of the material can decompose under physiological conditions within a desired period of time, such as on the order of minutes, hours, days, or weeks, depending on the exact material.

As used herein, the term "physiological conditions" refer to conditions of temperature, pH, osmotic pressure, osmolality, oxidation and electrolyte concentration in vivo in a patient or subject at the site of administration, or the site of action. For example, physiological conditions generally mean pH at about 6 to 8 and temperature of about 37° C. in the presence of serum or other body fluids.

As used herein, the term "near infrared light" refers to electromagnetic radiation having a wavelength within the range of 750 nm to about 2500 nm of the electromagnetic spectrum.

As used herein, the term "visible light" corresponds to electromagnetic radiation that can be detected by the human eye—i.e., electromagnetic radiation with a wavelength of approximately 390 to 750 nm in the electromagnetic spectrum.

As used herein, the term "ultraviolet light" refers to electromagnetic radiation whose wavelength is in the range from about 80 nm to about 390 nm.

As used herein, the term "administer" refers to the placement of a composition into a subject by a method or route which results in at least partial localization of the composition at a desired site such that desired effect is produced.

As used herein, the phrase "therapeutically-effective amount" or "effective amount" means that amount of a composition comprising a high molecular weight gelatin-DOX conjugate, which is effective for producing some desired therapeutic effect in at least a sub-population of cells in a subject at a reasonable benefit/risk ratio applicable to any medical treatment. For example, an amount of a composition comprising a high molecular weight gelatin-DOX conjugate administered to a subject that is sufficient to produce a statistically significant, measurable change in at least one symptom of a cancer (e.g., tumor size reduction).

As used herein, the term "cancer" refers to an uncontrolled growth of cells which interferes with the normal functioning of the bodily organs and systems. A subject who has a cancer is a subject having objectively measurable cancer cells present in the subject's body. Included in this definition are benign and malignant cancers, premalignant lesions, as well as dormant tumors or micrometastases. Cancers which migrate from their original location and seed vital organs can eventually lead to the death of the subject through the functional deterioration of the affected organs.

As used herein, the terms "treat", "treatment", or "treating" refer to therapeutic treatment, wherein the objective is to slow down (lessen) an undesired physiological change or disorder, such as the progression of cancer. Beneficial or desired clinical results can include, but are not limited to, tumor size reduction, reduction of the metastatic potential of the cancer, alleviation of symptoms, diminishment of extent of cancer, stabilized (i.e., not worsening) state of tumor, delay or slowing of cancer progression, amelioration or palliation of cancer, and remission (whether partial or total), whether detectable or undetectable. Any particular treatment regimen can provide one or more such clinical results in one or more patients, and need not provide all such clinical results. "Treatment" can also mean prolonging survival as compared to expected survival if not receiving treatment. For example, a treatment is considered effective for a subject if the tumor size is reduced by at least 10%, at least 20%, at least 30%, at least 40%, at least 50%, at least 60%, at least 70%, at least 80%, at least 90%, or more, after the treatment.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of tumors.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. In some embodiments, a straight chain or branched chain alkyl has 5 or fewer carbon atoms, 10 or fewer carbon atoms, or 15 or fewer carbon atoms.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups. In some embodiments, the heteroalkyl has 5 or fewer carbon atoms, 10 or fewer carbon atoms, or 15 or fewer carbon atoms.

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. An aryl group can comprise a 4-atom ring, a 5-atom ring, a 6-atom ring, a 7-atom ring, a 8-atom ring, a 9 atom ring, or more. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c] pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo [1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

Other than in the operating examples, or where otherwise indicated, all numbers expressing quantities of ingredients or reaction conditions used herein should be understood as modified in all instances by the term "about." The term "about" when used in connection with percentages may mean ±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology described herein is further illustrated by the following examples which in no way should be construed as being further limiting.

Example 1. A Synthesis Methodology for Preparing High Molecular Weight Gelatin-DOX Compounds High molecular weight gelatin-DOX compounds can be prepared in the following steps:

Step 1. Prepare amino group blocked doxorubicin (BDox) [Nagy A., et al (1996). Proc. Natl. Acad. Sci. USA: 93, 7269-73]: Dox HCl salt (50 mg, 86, umol) is dissolved in 1 mL of N,N-dimethylformamide (DMF), and Fmoc-OSu (30 mg, 90 umol) is added, followed by 30 uL (172 umol) of N,Ndiisopropylethylamine (DIPEA) with protection from light. After 3 hr the solvent is evaporated in vacuo, and the residue is crystallized by trituration from 0.1% aqueous trifluoroacetic acid (TFA) (vol/vol). The crystals are collected by filtration and washed once with cold diethyl ether to remove traces of excess Fmoc-OSu. Dry in a desiccator to obtain about 62 mg of BDOX.

Step 2. Prepare BDox-hydrazine (BDoxHZ): The above BDOX is reacted in 2 mL DMF with a 10 fold molar excess of HZ with 25 µL of glacial acetic acid and 200 mg of anhydrous sodium sulfate for 48 hr with mild stirring and protection from light. The sodium sulfate is removed by filtration and the filtrate solution is passed through a gel permeation chromatography (GPC) column of Styragel HR 1 in DMF to collect BDoxHZ separated from HZ. The solvent is evaporated in vacuo.

Step 3. Prepare BDOXHZ-glycylglycine (BDoxHZgg): An equimolar (to the BDoxHZ) amount of gg is added to two mL of DMF in solution. The above BDoxHZ is added to the gg/DMF solution with mild stirring for 1 hr. A 1.25 molar excess of dicyclocarbodiimide (DCC) is added and reacted for 2 hours with protection from light. Collect the BDoxHZgg by GPC and in vacuo as above.

Step 4. Prepare BDoxHZgg-gelatin (BDoxHZggG): The above BDoxHZgg is added to 4 mL of previously solvated and dissolved 40 mg of gelatin in formamide (FAM) at pH 6 with mild stirring for 1 hr and protection from light. Then 1.25 molar excess to gelatin carboxylic acid groups of 1-Ethyl-3-(3-dimethylaminopropyl)carbodiimide (EDC) is added and reacted for 2 hr at pH 6. Transfer reaction volume to a 50 mL centrifuge tube. Add ice-cold absolute ethanol to bring volume to 50 mL to precipitate BDoxHZggG. Spin 2000 rpm for 15 min at 15° C. Remove ethanol, redissolve in 4 mL of $H_2O$ with 200 mg of sodium chloride. Add ice-cold absolute ethanol as above to precipitate product. Hydrate and dissolve product in 4 mL FAM Step 5. Deblock BDoxHZggG to make conjugate (GDox): To the above FAM solution of BDoxHZggG, add 1 mL of piperidine to make an 80/20 FAM/piperidine solution. React with mild stirring for 30 min. Transfer reaction volume to 50 mL centrifuge tube. Add ice-cold absolute ethanol to bring volume to 50 mL. Spin 2000 rpm for 15 min at 15° C. Remove ethanol, redissolve in 4 mL of $H_2O$. Perform 2 repeated precipitations with 4 mL of water and 200 mg of NaCl, followed by 2 additional precipitations without NaCl. After the last precipitation dissolve product in 8 mL of water. Lyophilize and store GDox at −20° C.

Example 2. Solid Phase Peptide Synthesis (SPSS) Starting with Glycylglycine

High molecular weight gelatin-DOX compounds can be prepared in the following steps:

Step 1. Resin-C-Gly-Gly-N: Using an SPSS resin compatible with formamide (FAM), stir resin in formamide at a concentration of 0.05 mg/mL for 30 min to allow for resin to swell. Add a 3 fold excess of glycylglycine to the linking group on the SPSS resin. Stir to dissolve. Add 4 fold molar excess of N,N-diisopropylethylamine (DIPEA) to resin linker. Add 2.9 molar excess of HBTU (N,N,N',N'-Tetramethyl-O-(1H-benzotriazol-1-yl)uronium hexafluorophosphate). Stir for 30 min. Remove solvent by vacuum filtration using a 0.2 µm pore size filter. Suspend in formamide and filter again. Wash once with methanol, once with dichloromethane, and once again with FAM. Resuspend in water and lyophilize to obtain a solid.

Step 2. Blocked gelatin: Hydrate gelatin over night in FAM at a concentration of 16 mg/mL. To solution add a 25× molar excess of citraconic anhydride to gelatin amine groups. Maintain pH between 8-9 for 1 hour. Transfer reaction volume to 50 mL centrifuge tube. Add ice cold absolute ethanol to bring volume to 50 mL. Spin 2000 rpm for 15 min at 15° C. Remove ethanol, redissolve in 4 mL of $H_2O$ and repeat ethanol precipitation and spin. Redissolve precipitate in 4-8 mL of $H_2O$ and lyophilize.

Step 3. Resin-Gly-Gly-Blocked Gelatin: Hydrate resin with the gly-gly dipeptide in FAM for 30 min. Add freeze dried blocked gelatin to resin suspension at a concentration of 2 groups of Gly-Gly to every gelatin carboxylic acid group. Add 4 fold molar excess of N,N-diisopropylethylamine (buffer/activator for peptide coupling) to gly-gly. Add 2.9 molar excess of HBTU (N,N,N',N'-Tetramethyl-O-(1H-benzotriazol-1-yl)uronium hexafluorophosphate) Stir for 30 min. Remove solvent by vacuum filtration using a 0.2 m pore size filter. Suspend in FAM and filter again. Wash once with methanol, once with dichloromethane, and once again with FAM. Resuspend in water and lyophilize.

Step 4. Cleavage of Gelatin-GlyGly, and Deblocking Gelatin: Hydrate and suspend resin-Gly-Gly-Gelatin in FAM. To mixture add 10 mL of 95:2.5:2.5 trifluoroacetic acid:water:triisopropyl silane for every 100 mg of resin. Stir 90 min. Remove solvent by vacuum filtration using a 0.2 µm pore size filter. Collect filtrate. Wash again with the 95:2.5:2.5 cleavage cocktail and collect filtrate. Add methyl tertiary butyl ether (MTBE) to precipitate deblocked Gel-Gly-Gly. Dissolve precipitate in water and lyophilize.

Step 5. Gel-Gly-Gly-Hz: Dissolve Gel-Gly-Gly in FAM at a concentration of 16 mg/mL with hydrazine at a concentration of 20 moles of hydrazine to 1 mole of Gel COOH. Add 4 fold molar excess of N,N-diisopropylethylamine (buffer/activator for peptide coupling) to gly-gly. Add 2.9 molar excess of HBTU (N,N,N',N'-Tetramethyl-O-(1H-benzotriazol-1-yl)uronium hexafluorophosphate) Stir for 30 min. Transfer reaction volume to 50 mL centrifuge tube. Add ice-cold absolute ethanol to bring volume to 50 mL. Spin 2000 rpm for 15 min. Remove ethanol, redissolve in 4 mL of $H_2O$ and repeat ethanol precipitation and spin. Redissolve precipitate in 4-8 mL of $H_2O$ and lyophilize.

Step 6. Gel-Gly-Gly-Hz-Dox (GDox): Dissolve Gel-Gly-Gly-Hz in FAM at a concentration of 10 mg/mL at pH 5 with 25 µL of glacial acetic acid and 200 mg of anhydrous sodium sulfate. Add 10× molar excess of Dox HCl to hydrazide groups. Maintain pH 5 with stirring for 24 hours with protection from light. Transfer reaction volume to 50 mL centrifuge tube. Add ice-cold absolute ethanol to bring volume to 50 mL. Spin 2000 rpm for 15 min at 15° C. Remove ethanol, redissolve in 4 mL of $H_2O$ with 200 mg of NaCl and repeat ethanol precipitation and spin. Dissolve again in 4 mL $H_2O$ with 200 mg of NaCl. Repeat dissolution and precipitation 2 more times with only water. For the 5th precipitation, redissolve precipitate in 4-8 mL of $H_2O$ and lyophilize.

Example 3. Preparation, Drug Release Model and Cell Toxicity of a High Molecular Weight Gelatin-Doxorubicin Conjugate Successful synthesis of a high molecular weight (>100 kDa) gelatin doxorubicin conjugate (GDox) was achieved. A 53% release at pH 4.8 vs. 7% release at pH 7.4 was shown. This pH dependent release indicates the presence of the hydrazone bond between gelatin and doxorubicin (DOX) and demonstrates potential for limited release in the blood and selective release in the acid pH of the tumor and within cells. A model of DOX release from this conjugate is proposed that incorporates release at different pH as well as drug degradation, drug non-specific binding to gelatin and reversible release at acid pH. GDox shows cytotoxic activity in MCF7 and PC3 cancer cell lines. In vivo, a high molecular weight GDox should show selective tumor uptake by the EPR effect and increased exposure of tumor tissue to DOX. The higher molecular weight should produce greater antitumor efficacy with lower toxic side effects compared to lower weight Dox conjugates as well as to the free drug.

Materials

Type B bovine gelatin was supplied by Kind and Knox (Gelita USA, Sargent Bluff, Iowa). Doxorubicin-HCl (DOX) was from Bristol-Meyers Squibb. Glycylglycine (GG), 1-ethyl-3-(3-dimethylaminopropyl) carbodiimide HCl (EDC), hydrazine hydrate, formamide, p-nitrobenzaldehyde, dimethylformamide, acetyl hydrazide, sodium azide, sodium laurel sulfate, Dulbecco's phosphate buffered saline, RPMI 1640, trypsin/EDTA, and antibiotic solution were purchased from Sigma-Aldrich (St. Louis, Mo.). PC3 and MCF7 cell lines and EMEM media were purchased from ATCC (Manassas, Va.). Buffer salts, 0.2 µm syringe filters, and miscellaneous cell culture supplies were purchased from Fisher (Pittsburgh, Pa.).

Gelatin Doxorubicin Conjugate Synthesis

Gelatin was solvated over night at a concentration of 96 mg of gelatin in 4 mL of formamide, dissolved at 65° C. for 2 minutes followed by adjustment to pH 7. A solution of glycylglycine in 4 mL of formamide at a concentration of 2 times the moles of gelatin carboxylic acid groups (30.5 mg) was prepared by adjustment to pH of 3 and stirred. Following dissolution, the pH was adjusted to 7 and the GG solution was added to the gelatin solution at pH 7 for 1 hr with stirring at room temperature. A 1.1 fold molar excess of EDC (24.6 mg) to gelatin carboxyl groups was added and stirred at pH 7 for 3 hours at room temperature. The solution was placed into a 50 mL polypropylene centrifuge tube and ice cold absolute ethanol was added to bring the volume to 50 mL. Upon warming to room temperature the precipitate appeared and was centrifuged at 900×g for 15 minutes at 8° C. After decanting, the precipitate was dissolved in 4 mL of distilled water after hydration and brief heating at 65° C. Ice-cold absolute ethanol was again added with 200 mg of NaCl. Upon warming at room temperature, the precipitate was spun at 900×g for 15 minutes at 8° C. After decanting, the precipitate was dissolved in 8 mL of distilled water as described above, then lyophilized for subsequent addition. To a solution of 6 mL of formamide, 132 µL of hydrazine hydrate, corresponding to 20 fold molar excess of the gelatin carboxyl groups, was added with an adjustment to pH 6 followed by addition to the gelatin-glycylglycine lyophilized powder. After dissolution with 2 minutes at 65° C., the reaction was stirred at pH 6 for 1 hour. A 1.25 molar excess of EDC (27.6 mg) to gelatin carboxyl groups was added and maintained at pH 6 for 3 hours. The gelatin-glycylglycine-hydrazide (Gel-GG-Hz, precursor) was collected by the ethanol precipitation described above, lyophilized and stored at −20° C. The hydrazide content of Gel-GG-Hz was determined by the p-nitrobenzaldehyde assay described below.

Gel-GG-Hz was dissolved in 6 mL of formamide at a concentration of 10 mg/mL with 25 µL glacial acetic acid and 200 mg of anhydrous sodium sulfate at a pH of 5. A 10 fold molar excess of DOX (86.5 mg) to hydrazide groups was added and pH of 5 maintained with stirring for 24 hours in the dark. The reaction volume was then transferred to a 50 mL centrifuge tube for 5 repeated ethanol precipitations as described above with adjustment to pH 7 if needed after dissolution in water.

Molecular Weight and Mass Determination by Size Exclusion Chromatography

Molecular weight and mass determination of gelatin as well as GDox and its precursors were determined by modifying a previously reported protocol (22, 23) using a Waters HPLC system with a Phenomenex BioSep SEC s4000 column, a mobile phase of 100 mM sodium phosphate with 0.4% sodium laurel sulfate at pH of 7.4 and a flow rate of 0.5 mL per minute at 40° C. Samples for analysis were dissolved in 100 mM sodium phosphate, pH 7.4, with 0.025% sodium azide at an approximate concentration of 0.5 mg/mL, heated at 65° C. for 2 min, then filtered with a 0.2 µm syringe filter. Ten microliters of the samples were injected for a run time of 30 minutes with UV detection at 214 nm. Molecular weight of gelatin or conjugate was calculated using standard curve of polystyrene sulfonate standards ranging from 10.6 kDa to 282 kDa. Concentration of gelatin in an unknown solid mixture was determined from area under the curve of the chromatogram using a standard curve of AUC vs. known gelatin concentrations ranging from 0.1 mg/mL to 0.6 mg/mL.

Hydrazide Assay

The hydrazine content on the precursor was determined as described previously (23). Briefly, following a mass determination by HPLC SEC, the precursor was dissolved from 0.025 mg/mL to 0.2 mg/mL in 1.365 mL of pH 5 100 mM acetate buffer. To each solution, 135 µL of 5 mM p-nitrobenzaldehyde in dimethylformamide was added, then were incubated at 37° C. for 3 hours and measured for UV absorbance at 340 nm. Concentration of the hydrazone formed was determined using an extinction coefficient of 16,800 $M^{-1}cm^{-1}$. The concentration of hydrazide groups was adjusted to account for a 41% complete reaction determined previously. The determined number of hydrazide groups on a Gel-GG-Hz (precursor) is reported as moles of hydrazide per mole of gelatin of an average molecular weight of 159,000 g/mol.

Doxorubicin Drug Load

After accurately determining the concentration of GDox in the solid lyophilized product, 2 mg of GDox was dissolved in 5 mL of 0.1 M potassium phosphate buffer pH 4.8. Absorbance at 488 was measured and concentration of doxorubicin was determined by the standard curve: $ABS_{488}=19.161[Dox](mg/mL)+0.0152$. After subtracting the contribution of doxorubicin absorption at 220 nm by the standard curve $ABS_{220}=38.126[Dox](mg/mL)+0.0337$, absorbance at 220 nm was measured, and gelatin concentration was calculated by the standard curve: $ABS_{220}=9.2113[Gel](mg/mL)+0.0219$. The doxorubicin load was calculated by dividing the mass of doxorubicin by the mass of gelatin plus the mass of doxorubicin and reported as a weight by weight percentage.

Doxorubicin Release from GDox

The release design was described previously (23). Briefly, GDox was dissolved at 1 mg/mL in 0.03 M sodium phosphate with 0.12 M sodium chloride at pH 4.8, 6.5 and 7.4 in 50 mL polypropylene centrifuge tubes. GDox solution (110 µL) was placed into individual siliconized polypropylene microcentrifuge tubes, and then incubated at 37° C. for 0, 3, 8, 24 and 48 hr. At each time point 100 µL of the release solution was removed and placed into a new microcentrifuge tube with 100 µL of a 0.025 mg/mL solution of daunorubicin as an internal standard. One mL of ice cold absolute ethanol was added, and the samples were centrifuged at 12,000×g for 10 min. One mL of the supernatant was transferred into a glass centrifuge tube and 200 μL of a 1 M sodium phosphate buffer, pH 8.5, was added followed by 2.8 mL of dichloromethane. The test tubes were then shaken for 10 minutes, centrifuged at 1600×g for 5 minutes, and 3 mL of the lower organic layer were removed and placed into glass test tubes with screw caps. The dichloromethane was evaporated at 30° C. under nitrogen and samples were stored at −70° C. until analysis.

Released DOX was assayed as described previously (24). A Shimadzu HPLC system was used with a C18 Phenomenex Nucleosil column with a 10 μm particle size, and at 100 Å pore size. The mobile phase was 65/35% v/v methanol: 0.01 M sodium phosphate, pH 3, at a flow rate of 2 mL/min. A fluorescence detector was used at an excitation wavelength of 470 nm and an emission detection of 555 nm. The injection volume was 10 μL and run time was 10 minutes. Concentration of DOX released was determined from standard curves ranging from 1 μg/mL to 100 μg/mL prepared with 1 mg/mL gelatin using the same extraction procedure for the release samples.

Cell Culture

MCF7 cells were maintained in EMEM growth media with 10% fetal bovine serum and 0.01 mg/mL recombinant human insulin. Growth inhibition experiments were performed in the above media with the addition of penicillin at 100 units/mL and streptomycin at 0.1 mg/mL. PC3 cells were maintained in RPMI 1640 with 10% fetal bovine serum with penicillin and streptomycin at the above concentrations for growth inhibition experiments. Cells were grown in 75 cm² flasks at 37° C. with 5% $CO_2$. They were routinely passed once achieving 85% confluence by rinsing 3 times with 5 mL Dulbecco's PBS and detached using 2 mL of trypsin/EDTA solution. Cells were resuspended in fresh growth medium and seeded at either $1 \times 10^5$ cells (PC3) or $1 \times 10^6$ cells (MCF7).

Cell Growth Inhibition

Cells were plated at a 4,000 cells per well on two 96-well plates with vacuum-gas plasma treated surfaces. The plates were incubated at 37° C. 5% $CO_2$ for 24 hours to allow cell adherence, and one plate was assayed by AlamarBlue (see below) for the number of cells to be used as a starting point for growth inhibition. To the wells of the other plate, 50 μL of DOX, GDox in growth medium, or growth medium (control) were added to produce DOX or equivalent concentrations ranging from 0.001 μM to 100 μM for DOX and 0.01 μM to 20 μM for GDox in replicates of 5. Plates were then incubated at 37° C., 5% $CO_2$ for 72 hours.

Cell growth was determined by AlamarBlue assay following incubation. Growth medium with or without agent was removed and the wells were washed 3 times with 100 μL Dulbecco's phosphate buffered saline. Then, 250 μL of 10% AlamarBlue in growth medium with antibiotics was added. Initial fluorescence at 530/590 nm ($F_0$) was measured using a Perkin Elmer Victor3 1420 bench top plate reader. The percent growth value was obtained by dividing the fluorescence for the drug wells by the fluorescence for the control wells after subtracting the fluorescence from the 24 hr control plate from both.

Cell growth inhibition studies for both cell lines were conducted within 13 passages after thawing. Average percent growth at each doxorubicin concentration is the mean of 15 wells from 3 separate growth inhibition experiments conducted on separate days.

Curve Fitting and Statistics

Curve fitting for DOX release was performed using SigmaPlot 12.0 dynamic curve fitting function, fitting the data to single, double or triple exponential equations. Coefficient estimates and their t and p values were obtained from the program output. Coefficients were considered significant with p<0.05. Rate constants were calculated from the output parameters from the fitting program.

The concentration of DOX equivalent to achieve 50% growth ($IC_{50}$) for GDox and DOX were calculated using Sigma-Plot 12.0 dynamic curve fitting. The % growth vs. Log [DOX] equivalent concentration (μM) data was fit to a four parameter logistic curve reporting a minimum, maximum, Hillslope, and $IC_{50}$. Standard error of the $IC_{50}$ values were determined from the program output. A t-test was also used for tests of significance with p<0.05.

Results

The chemical structure for GDox is shown in FIG. 1. It shows a representative amino acid sequence of gelatin with a carboxyl group to which a glycylglycine linker with a hydrazone bond to doxorubicin is shown. Two batches of GDox were synthesized with the drug loads and yields reported in Table 1. The chromatogram generated by measuring DOX absorbance at 488 nm (data not shown), shows clear absorbance at the same retention times as gelatin peaks confirming the presence of DOX on gelatin.

Gelatin used for GDox synthesis is shown in FIG. 2A. The three predominant peaks of gelatin represent a 100 kDa specie (15.1 min), a 200 kDa specie (13.1 min), and the excluded volume corresponding to all species greater than 310 kDa (11.2 min). The large peak at 24 minutes represents salts of the sample solvent. The chromatogram of GDox in FIG. 2B shows the same three significant peaks for gelatin: one for the 100 kDa specie (15.6 min), one for the 200 kDa specie (13.7 min) one that corresponds to molecular weights >310 kDa (11.0 min). For comparison, the chromatogram of previously reported low molecular weight GDox in FIG. 2C shows significant degradation as there is no presence of the most abundant 100 kDa gelatin peak, and the predominant peaks in the low molecular weight conjugate correspond to molecular weights of 26 and 16 k Da (23).

Figures 3A, 3B, 3C, 3D:
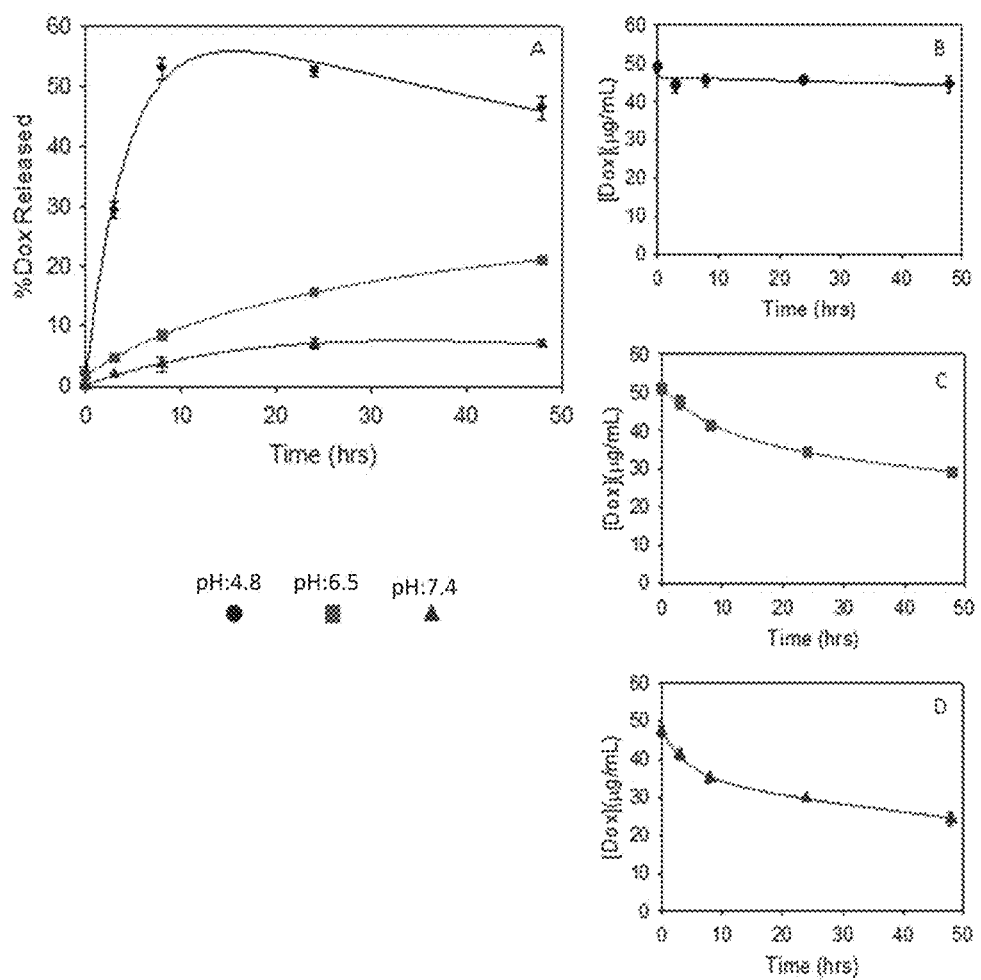
FIGS. 3A-3D are plots showing % Dox release of initial dox load of 4.26% of GDox with curve fitted lines (FIG. 3A) Mean±SD, n=4. Physical mix of dox and gel at: pH 4.8 (FIG. 3B), 6.5 (FIG. 3C) and 7.4 (FIG. 3D). Mean±SD, n=3.

Doxorubicin release from GDox at pH 4.8, 6.5 and 7.4 is shown in FIG. 3. At pH 4.8 DOX is released quickly, achieving 53±1.9% release of the total DOX load within 8 hours, followed by a small decrease. DOX release is lower at pH 6.5, continually increasing to 21±0.7% at the end of 48 hours. Release is even lower at pH 7.4 increasing to only 7±0.6% by 48 hours. Doxorubicin physically mixed with gelatin under the same conditions as the release experiment shows different behavior at each pH. The DOX concentration in solution decreases very slightly at pH 4.8. At pH 6.5 and 7.4, doxorubicin decline shows more loss with a steeper initial decline, followed by a shallower decline until the end of the experiment.

Figures 4A, 4B:
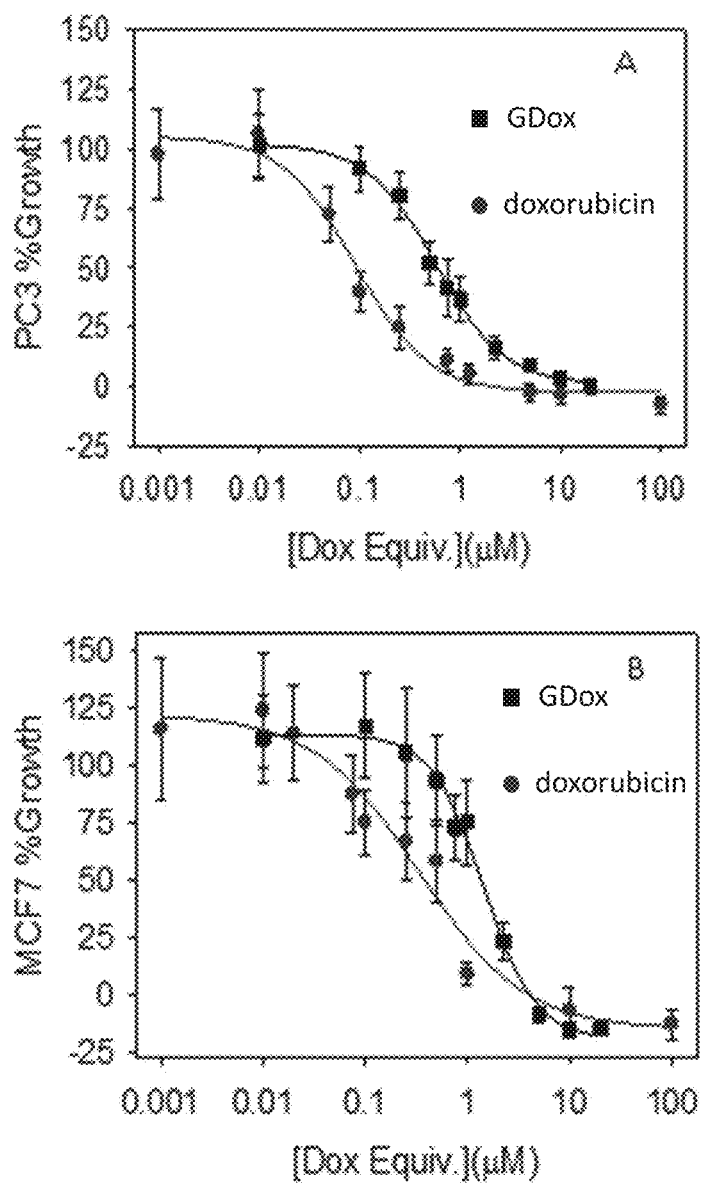
FIGS. 4A-4B are plots showing growth inhibition of PC3 (A) and MCF7 (B) cells by doxorubicin, and GDox. Mean±SD, n=15.

Growth inhibition profiles for PC3 and MCF7 cells are shown in FIG. 4. Doxorubicin and GDox both show growth inhibition upon PC3 and MCF7 cells. At high doxorubicin equivalent concentrations, cell growth becomes negative; indicating that there are fewer cells at the end of 72 hours of DOX incubation than there were at the beginning. $IC_{50}$ values for DOX and GDox for PC3 and MCF7 cell lines are shown in Table 2.

Discussion

GDox synthesis and its degradation were previously reported (23). Synthesis was conducted under aqueous conditions beginning with gelatin of a molecular weight of 159 kDa with blocked amino groups followed by additional steps using the carbodiimide, EDC, and separation steps using size exclusion chromatography resulting in a GDox molecular weight of approximately 22 kDa. Changing the reaction solvent to formamide and conducting EDC coupling reactions at an acid pH while also using ethanol precipitation for separation steps instead of size exclusion chromatography resulted in a high molecular weight GDox.

Producing a high molecular weight gelatin conjugate is important for successful delivery of the drug. It is anticipated that the high molecular weight will extend circulation time and allow greater accumulation within tumors from the EPR effect than would occur by lower molecular weights. Without wishing to be bound by theory, higher molecular weights correlate with circulation time and consequently with higher tumor uptake resulting in greater antitumor efficacy. The enhanced effect from higher molecular weight is anticipated to also be greater, and with substantially fewer side effects, than the effect of free drug administered alone.

The release experiments at various pH values demonstrate the acid lability of the bond between gelatin and DOX. The release at pH 4.8 and near absent release at pH 7.4 indicates a successful hydrazone conjugation of DOX to gelatin. The release behavior also demonstrates the potential benefits of GDox as a delivery system. The small amount of free drug release at pH 7.4 is anticipated to extend conjugate circulation time without meaningful release until accumulation in tumor tissue. The small DOX release at pH 7.4 is also anticipated to minimize toxic and life threatening side effects of the free drug. Once in the tumor and following cellular uptake into the lysosome environment at pH 4.8, DOX release is expected to be substantial.

The approximate 50% DOX release at pH 4.8 appears to be an important characteristic of this conjugate. A reversible release process is proposed whereby after DOX release, the hydrazone bond can be reformed between the now free gelatin hydrazide groups and DOX. Since pH 5 is used to add DOX during synthesis, it is likely that both release and covalent re-attachment occur during the release experiment in non-sink conditions.

The loss of DOX from the physical mixture with gelatin in solution is greatest at pH 7.4, less at 6.5 and the least at pH 4.8, which is consistent with previous reports of greater degradation at a higher pH (25, 26). During extraction of the physical mixture samples at pH 6.5 and 7.4, specifically during the ethanol precipitation step, an increase of red coloration of the gelatin precipitate was observed. Color increased throughout the 48 hours of the experiment and was absent at early time points. This suggests a slow non-specific binding between gelatin and DOX, as opposed to an immediate adsorption. At pH 4.8, the red coloration of the gelatin was not observed, indicating that the binding process is either minimal or absent. In addition, the lack of a logarithmic fit of the pH 6.5 and 7.5 data (not shown) as reported previously for DOX degradation (25) suggests that an additional process is occurring. Based on this information and reports of similar non-specific interactions between DOX and the carrier (27, 28), this behavior is hypothesized to also occur during DOX release from GDox.

The above observations allow for the following global model describing DOX amounts during GDox drug release, where $X_g$ is the amount of DOX on GDox, X is the amount of free DOX in solution, $X_{bind}$ is the amount of DOX non-specifically bound to gelatin. All k's are first order rate constants; where $k_1$ is DOX release, $k_2$ is DOX reacting with a free hydrazide group re-forming a hydrazone bond, $k_4$ is DOX non-specifically binding to gelatin, $k_3$ is DOX being freed of non-specific binding, and $k_d$ is the degradation rate constant.

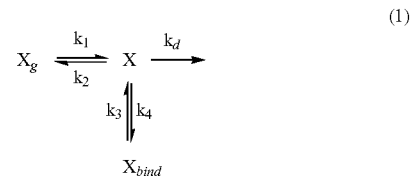

(1)

Two assumptions are present in this model. The first is that released DOX adsorbing to the container is near instantaneous and virtually negligible. The second assumption is that no burst release of DOX occurs from DOX adsorbed to GDox during preparation. This assumption is supported by the DOX release results at time zero that are not statistically different from zero.

Defining the rate laws for the model and integrating gives an equation for the amount of DOX in solution at time t:

$$X(t) = \frac{X_{g0}k_1(k_3 - a)}{(a-b)(a-c)}e^{-at} + \frac{X_{g0}k_1(k_3 - b)}{(a-b)(c-b)}e^{-bt} + \frac{X_{g0}k_1(k_3 - c)}{(a-c)(b-c)}e^{-ct} \quad (2)$$

$$a + b + c = k_1 + k_2 + k_3 + k_4 + k_d \quad (3)$$

$$ab + bc + ac = k_1k_3 + k_1k_4 + k_1k_d + k_2k_3 + k_3k_d \quad (4)$$

$$abc = k_1k_3k_d \quad (5)$$

At different pHs some processes may be diminished or absent within the scope of the release conditions. At pH 4.8, the physical mixture of doxorubicin and gelatin showed no evidence for non-specific binding of DOX with gelatin, thus, $k_3$ and $k_4$ are treated as insignificant during drug release at pH 4.8. The scheme and the equation for DOX released at time t takes the form of:

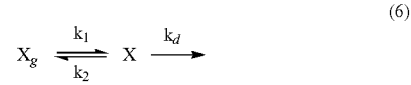

(6)

$$a + b = k_1 + k_2 + k_d \quad (7)$$

$$X(t) = \frac{X_{g0}k_1}{(b-a)}e^{-at} - \frac{X_{g0}k_1}{(b-a)}e^{-bt} \quad (8)$$

$$ab = k_1k_d \quad (9)$$

A pH of 6.5 is possibly acidic enough for DOX to react with free hydrazide groups, reforming the hydrazone bond. Also present is the non-specific binding to gelatin. For concentrations of DOX during drug release at pH 6.5, the release model includes all processes in Equation 1.

At a pH of 7.4, minimal reaction between free gelatin hydrazide groups and DOX is expected. The model can be slightly simplified by removal of $k_2$ taking the form:

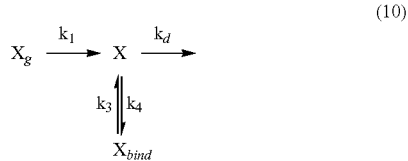
$$(10)$$

$$X(t) = \frac{X_{g0}k_1(k_3 - a)}{(a-b)(a-c)}e^{-at} + \frac{X_{g0}k_1(k_3 - b)}{(a-b)(c-b)}e^{-bt} + \frac{X_{g0}k_1(k_3 - c)}{(a-c)(b-c)}e^{-ct} \quad (11)$$

$$a + b + c = k_1 + k_2 + k_3 + k_4 + k_d \quad (12)$$

$$ab + bc + ac = k_1k_3 + k_1k_4 + k_1k_d + k_3k_d \quad (13)$$

$$abc = k_1k_3k_d \quad (14)$$

In a similar, but less complicated manner as above, equations describing loss of DOX once released from GDox at each pH (non-specific binding ($k_4$), de-binding ($k_3$), and degradation, ($k_d$)) can be derived based on the physical mixtures of DOX and gelatin. The model describing the loss of DOX from solutions of the physical mixture is:

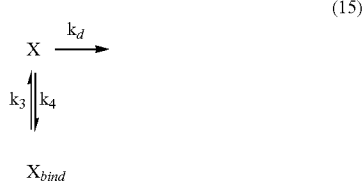
$$(15)$$

$$X(t) = \frac{X_0(k_3 - a)}{(b-a)}e^{-at} + \frac{X_0(k_3 - b)}{(a-b)}e^{-bt} \quad (16)$$

$$a + b = k_3 + k_4 + k_d \quad (17)$$

$$ab = k_3k_d \quad (18)$$

As noted above, non-specific binding to gelatin is not expected at pH 4.8. The model for DOX loss at pH 4.8 becomes a first order process:

$$X \xrightarrow{k_d} \quad (19)$$

$$X = X_0 e^{-k_d t} \quad (20)$$

Table 3 shows the equations obtained from curve fitting results of DOX amounts in solution during release from GDox or mixed with gelatin. All equations have $R^2$ values ≥0.95 except for the mixture at pH 4.8. The obtained coefficients are statistically significant (p<0.05) for the physical mixtures. However, the coefficients only have statistical significance for DOX release at pH 4.8, not release at pH 6.5 or 7.4.

The calculated rate constants from the significant coefficients of the fitted equations are shown in Table 4. The increase of $k_d$ with an increase in pH for the physical mixtures of DOX and gelatin as well as the magnitude of $k_d$ values are similar to findings from other reports (25, 26). The higher $k_4$ value for 7.4 indicates a faster non-specific binding process to gelatin than at pH 6.5. However, the calculated $k_d$ from the release data at pH 4.8 is an order of magnitude larger than that calculated from the physical mixture data. This difference is ascribed to insufficient time for DOX release to achieve equilibrium with its covalent reattachment to hydrazine groups whereby the only change in solution is due to degradation.

The $IC_{50}$ values for DOX in PC3 and MCF7 cells are similar to those reported elsewhere (29, 30). The higher $IC_{50}$ of GDox for MCF7 and PC3 cells than that of free DOX is expected. Doxorubicin is lipid permeable and can quickly diffuse through the cell membrane (31-33) whereas on GDox, the DOX is bound to a large molecular weight protein and will not enter the cell through permeation. Other macromolecular DOX delivery systems have shown similar behavior (31, 34). The $IC_{50}$ for the low molecular weight GDox reported previously of 0.75±0.36 μM (23) for PC3 cells is not statistically different from the $IC_{50}$ obtained from the high molecular weight GDox (of 0.57 μM) in this study (p=0.33). One possible, but not exclusive, explanation for this similar viability is that cellular uptake of the conjugate is not dependent on molecular weight of the carrier.

Successful synthesis of a high molecular weight gelatin doxorubicin conjugate was achieved. Release studies indicate the presence of the hydrazone bond between gelatin and DOX and demonstrate potential for limited release in the blood and selective release in the acid pH of the tumor and within cells. A model of DOX release from this conjugate is proposed that incorporates release at different pH as well as drug degradation, drug non-specific binding to gelatin and reversible release at acid pH. While others have shown the validity of a reversible drug release model (35), the model proposed here has the advantage of identifying the individual processes. GDox shows cytotoxic activity in MCF7 and PC3 cancer cell lines. The gelatin used in GDox has an average molecular weight greater than 150 kDa. This size is well over the renal excretion threshold (about 40 kDa, see Tanner et al., Am. J. Physiol. Renal Physiol. 2009, 296, F1269-1278), and should increase plasma half-life and EPR induced cancer uptake for the conjugate as well as preventing unwanted uptake of doxorubicin into cardiac tissue. In vivo, the high molecular weight GDox should show selective tumor uptake by the EPR effect and increased overall exposure of tumor tissue to DOX.

TABLE 1

Properties the GDox conjugate synthesized from the same precursor

| | Hzide Groups/ mol gelatin | Dox % w/w | Mass |
|---|---|---|---|
| Batch 1 | 59.3 ± 2.3 | 4.3% | 28.0 mg |
| Batch 2 | 59.3 ± 2.3 | 5.3% | 26.6 mg |

TABLE 2

Doxorubicin and GDox IC50 values for PC3 and MCF7 cell lines. Mean ± SD, of 3 experiments with replicates of 5 wells.

| Cell Line | Dox (µM) | High MW GDox (µM) |
|---|---|---|
| PC3 | 0.09 ± 0.038 | 0.57 ± 0.10 |
| MCF7 | 0.336 ± 0.251 | 1.44 ± 0.31 |

TABLE 3

Equations obtained from curve fitting for change of DOX amount in solution during release from conjugate or physical mix with gelatin$^a$.

| pH | DOX Release | Physical Mixture |
|---|---|---|
| 4.8 | $X(t) = -3.07e^{-0.245t} + 2.99e^{-0.007t}$ | $X(t) = 5.12e^{-0.001t}$ |
| 6.5 | $X(t) = -0.288e^{-0.120t} - 3.74e^{-0.012t} + 4.10e^{-0.006t}$ | $X(t) = 1.49e^{-0.120t} + 4.42e^{-0.006t}$ |
| 7.4 | $X(t) = -3.57e^{-0.120t} + 3.14e^{-0.128t} + 0.44e^{-0.006t}$ | $X(t) = 1.33e^{-0.242t} + 3.96e^{-0.008t}$ |

$^a$All equations have $R^2$ values ≥0.95 except for the mixture at pH 4.8.

TABLE 4

Rate constants calculated from significant coefficients from the equations from SigmaPlot.

Rate Constants from phisical mix (1 hr)

| pH | $k_3$ | $k_4$ | $k_d$ |
|---|---|---|---|
| 6.5 | 0.091 | 0.027 | 0.008 |
| 7.4 | 0.183 | 0.056 | 0.011 |

Rate constants from release (1/hr)

| pH | $k_1$ | $k_2$ | $k_d$ |
|---|---|---|---|
| 4.8 | 0.141 | 0.099 | 0.012 |

REFERENCES FOR EXAMPLE 3

1. Barenholz, Y. C. (2012) Doxil®—the first FDA-approved nano-drug: lessons learned, *Journal of Controlled Release* 160, 117-134.
2. Hortobagyi, G. (1997) Anthracyclines in the treatment of cancer, *Drugs* 54, 1-7.
3. Weiss, R. B. (1992) The anthracyclines: will we ever find a better doxorubicin?, In *Seminars in Oncology*, pp 670-686.
4. Ewer, M. S., Martin, F. J., Henderson, I. C., Shapiro, C. L., Benjamin, R. S., and Gabizon, A. A. (2004) Cardiac Safety of Liposomal Anthracyclines, *Seminars in Oncology* 31, 161-181.
5. Kataoka, K., Matsumoto, T., Yokoyama, M., Okano, T., Sakurai, Y., Fukushima, S., Okamoto, K., and Kwon, G. S. (2000) Doxorubicin-loaded poly(ethylene glycol)-poly(B-benzyl-L-aspartate) copolymer micelles: their pharmaceutical characteristics and biological significance, *Journal of Controlled Release* 64, 145-153.
6. Duncan, R. (1999) Polymer conjugates for tumour targeting and intracytoplasmic delivery. The EPR effect as a common gateway?, *Pharmaceutical Science and Technology Today* 2, 441-449.
7. Das, A., Durrant, D., Mitchell, C., Mayton, E., Hoke, N. N., Salloum, F. N., Park, M. A., Qureshi, I., Lee, R., Dent, P., and Kukreja, R. C. (2010) Sildenafil increases chemotherapeutic efficacy of doxorubicin in prostate cancer and ameliorates cardiac dystunction *Proceedings of the National Academy of Sciences* 107, 18202-18207.
8. Goren, D., Horowitz, A. T., Tzemach, D., Tarshish, M., Zalipsky, S., and Gabizon, A. (2000) Nulcear Delivery of Doxorubicin via Folate-targeted Liposomes with Bypass of Multidrug-resistance Efflux Pump, *Clinical Cancer Research* 6, 1949-1957.
9. Duncan, R. (2006) Polymer conjugates as anticancer nanomedicines, *Nature Reviews Cancer* 6, 688-701.
10. Duncan, R. (2003) The Dawning Era of Polymer Therapeutics, *Nature Reviews Drug Discovery* 2, 347-360.
11. Vicent, M. J., and Duncan, R. (2006) Polymer conjugates: nanosized medicines for treating cancer, *Trends in biotechnology* 24, 39-47.
12. Li, C., and Wallace, S. (2008) Polymer-drug conjugates: Recent development in clinical oncology, *Advanced Drug Delivery Reviews* 60, 886-898.
13. Lee, C. H., Singla, A., and Lee, Y. (2001) Biomedical applications of collagen, *International Journal of Pharmaceutics* 221, 1-22.
14. Balakrishnan, B., Mohanty, M., Umashankar, P., and Jayakrishnan, A. (2005) Evaluation of an in situ forming hydrogel wound dressing based on oxidized alginate and gelatin, *Biomaterials* 26, 6335-6342.
15. Levi, M., and de Jonge, E. (2007) Clinical relevance of the effects of plasma expanders on coagulation, In *Seminars in thrombosis and hemostasis*, pp 810-815, © Thieme Medical Publishers.
16. Lee, E. S., Gao, Z., and Bae, Y. H. (2008) Recent progress in tumor pH targeting nanotechnology, *Journal of Controlled Release* 132, 164-170.
17. Zhang, X., Lin, Y., and Gillies, R. J. (2010) Tumor pH and its measurement, *Journal of Nuclear Medicine* 51, 1167-1170.
18. Zhu, S., Hong, M., Tang, G., Qian, L., Lin, J., Jiang, Y., and Pei, Y. (2010) Partly PEGylated polyamidoamine dendrimer for tumor-selective targeting of doxorubicin: The effects of PEGylation degree and drug conjugation style, *Biomaterials* 31, 1360-1371.
19. Etrych, T., Jalinkova, M., Rihova, B., and Ulbrich, K. (2001) New HPMA copolymers containing doxorubicin bound via pH-sensitive linkage: synthesis and preliminary in vitro and in vivo biological properties, *Journal of Controlled Release* 73, 89-102.
20. Kaneko, T., Willner, D., Monkovic, I., Knipe, J. O., Braslawsky, G. R., Greenfield, R. S., and Vyas, D. M. (1991) New Hydrazone Derivatives of Adriamycin and Their Immunoconjugates—a Correlation between Acid Stability and Cytotoxicity *Bioconjugate Chemistry* 2, 133-141.
21. Sirova, M., Mrkvan, T., Etrych, T., Chytil, P., Rossmann, P., Ibrahimova, M., Kovar, L., Ulbrich, K., and Rihova, B. (2010) Preclinical Evaluation of Linear HPMA-Doxorubicin Conjugates with pH-Sensitive Drug Release: Efficacy, Safety, and Immunomodulating Activity in Murine Model, *Pharmaceutical Research* 27, 200-208.
22. Dupont, A.-L. (2002) Study of the degradation of gelatin in paper upon aging using aqueous size-exclusion chromatography, *Journal of Chromatography A* 950, 113-124.
23. Wu, D. C., Cammarata, C. R., Park, H. J., Rhodes, B. T., and Ofner, C. M., 3rd. (2013) Preparation, drug release, and cell growth inhibition of a gelatin: doxorubicin conjugate, *Pharm Res* 30, 2087-2096.
24. Álvarez-Cedrón, L., Sayalero, M. L., and Lanao, J. M. (1999) High-performance liquid chromatographic validated assay of doxorubicin in rat plasma and tissues, Journal of Chromatography B: Biomedical Sciences and Applications 721, 271-278.

25. Wu, D. C., and Ofner, C. M., 3rd. (2013) Adsorption and degradation of doxorubicin from aqueous solution in polypropylene containers, *AAPS PharmSciTech* 14, 74-77.
26. Beijnen, J., Van der Houwen, O., and Underberg, W. (1986) Aspects of the degradation kinetics of doxorubicin in aqueous solution, *International Journal of Pharmaceutics* 32, 123-131.
27. Stefano, G. D., Lanza, M., Kratz, F., Merina, L., and Fiume, L. (2004) A novel method for coupling doxorubicin to lactosaminated human albumin by an acid sensitive hydrazone bond: synthesis, characterization and preliminary biological properties of the conjugate, *European journal of pharmaceutical sciences* 23, 393-397.
28. Hrubý, M., Koňák, Č., and Ulbrich, K. (2005) Polymeric micellar pH-sensitive drug delivery system for doxorubicin, *Journal of Controlled Release* 103, 137-148.
29. Taylor, C., Dalton, W., Parrish, P., Gleason, M., Bellamy, W., Thompson, F., Roe, D., and Trent, J. (1991) Different mechanisms of decreased drug accumulation in doxorubicin and mitoxantrone resistant variants of the MCF7 human breast cancer cell line, *Br J Cancer* 63, 923-929.
30. Pinto, A. C., Moreira, J. N., and Simoes, S. (2009) Ciprofloxacin sensitizes hormone-refractory prostate cancer cell lines to doxorubicin and docetaxel treatment on a schedule-dependent manner, *Cancer Chemotherapy and Pharmacology* 64, 445-454.
31. Goren, D., Horowitz, A. T., Tzemach, D., Tarshish, M., Zalipsky, S., and Gabizon, A. (2000) Nuclear delivery of doxorubicin via folate-targeted liposomes with bypass of multidrug-resistance efflux pump, *Clinical Cancer Research* 6, 1949-1957.
32. Durand, R. E., and Olive, P. L. (1981) Flow cytometry studies of intracellular adriamycin in single cells in vitro, *Cancer Research* 41, 3489-3494.
33. Hovorka, O., St'astny, M., Etrych, T., Subr, V., Strohalm, J., Ulbrich, K., and Rihova, B. (2002) Difference in the intracellular fate of free and polymer-bound doxorubicin, *Journal of Controlled Release* 80, 101-117.
34. Ye, W. L., Teng, Z. H., Liu, D. Z., Cui, H., Liu, M., Cheng, Y., Yang, T. H., Mei, Q. B., and Zhou, S. Y. (2013) Synthesis of a new pH-sensitive folate-doxorubicin conjugate and its antitumor activity in vitro, *Journal of Pharmaceutical Sciences* 102, 530-540.
35. Zeng, L., An, L., and Wu, X. (2011) Modeling drug-carrier interaction in the drug release from nanocarriers, *J Drug Deliv* 2011, 370308.

Example 4. Stability of High Molecular Weight Gelatin-Doxorubicin Conjugates in Serum The conjugate showed very little degradation into lower molecular weight species during exposure to serum containing general enzymes. This study was conducted to confirm the expectation that the gelatin-doxorubicin conjugate (GDox) would maintain its high molecular weight in the circulation to allow long times for tumor accumulation.

Materials

The gelatin-doxorubicin conjugate was synthesized as described above in Example 3. Phosphate buffered saline (PBS) and sodium lauryl sulfate were obtained from Sigma-Aldrich (St. Louis, Mo.), fetal bovine serum (FBS) was obtained from ATCC (Manassas, Va.), and Buffer salts, 0.2 μm syringe filters, and miscellaneous supplies were purchased from Fisher (Pittsburgh, Pa.).

Evaluation of GDox Stability in Buffer and Serum

Into four mL of PBS or FBS, 4 mg of GDox was dissolved with stirring. The solution was maintained at 37° C. and pH 7.4 for the duration of the experiment. At times 0, 3, 6, 12, and 24 hrs, a 0.3 mL sample was removed and prepared for HPSEC analysis. Samples were prepared by adding 0.3 mL of 100 mM sodium phosphate, pH 7.4, with 0.025% sodium azide, filtering with a 0.2 micron syringe filter, and placing 50 microliters into an insert for placement in a vial for assay.

HPSEC Assay and Chromatograms for Determination of Degradation

Molecular weight and molecular distribution of GDox were determined by the procedure above in example 3 using a Waters HPLC system with a Phenomenex BioSep SEC s4000 column, a mobile phase of 100 mM sodium phosphate with 0.4% sodium laurel sulfate at pH of 7.4, and a flow rate of 0.5 ml per minute at 40° C. Ten microliters of the samples were injected for a run time of 30 minutes with VIS detection at 488 nm. The molecular weight of gelatin or conjugate was calculated using a standard curve of polystyrene sulfonate standards ranging from 10.6 kDa to 282 kDa. The degradation was followed by HPSEC chromatogram shifts to lower molecular weights. The low molecular weight percent (% LMW) was calculated as the area of species less than 100 kDa expressed as a percent of the total area from all species.

Results

Figure 5A:
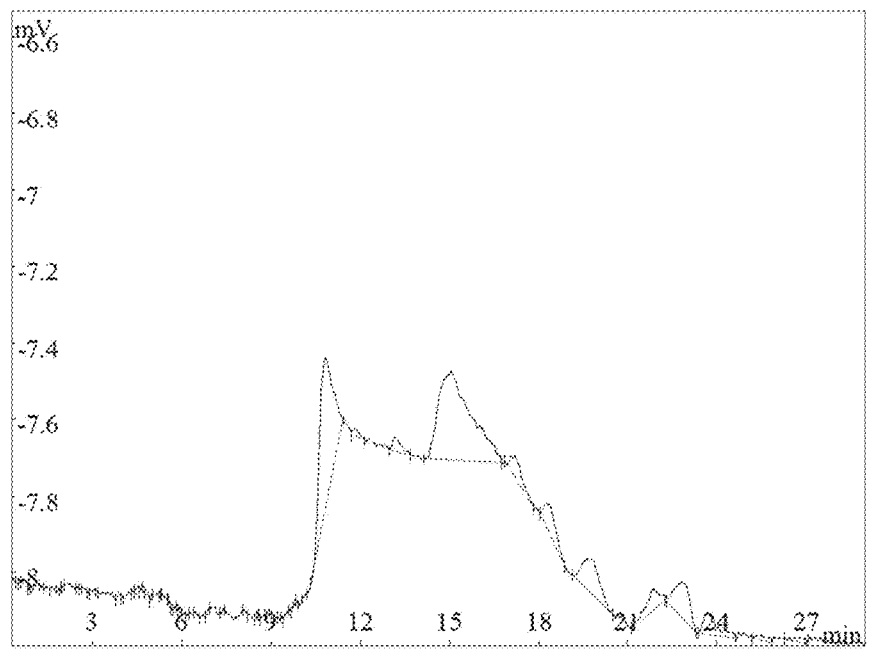
FIGS. 5A-5D show that gelatin-DOX conjugate are stable in serum.
Figure 5B:
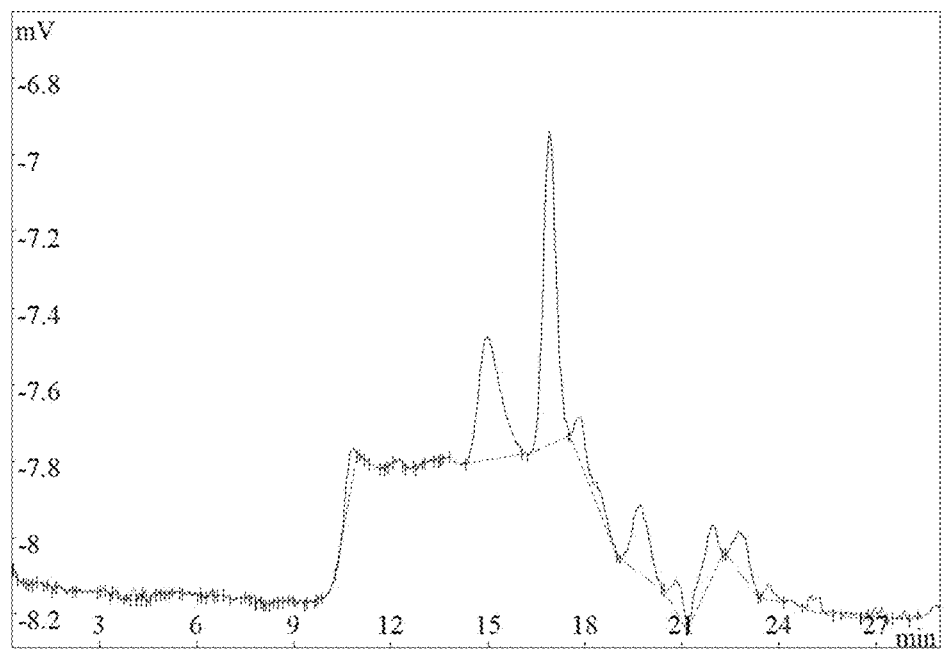
Figure 5C:
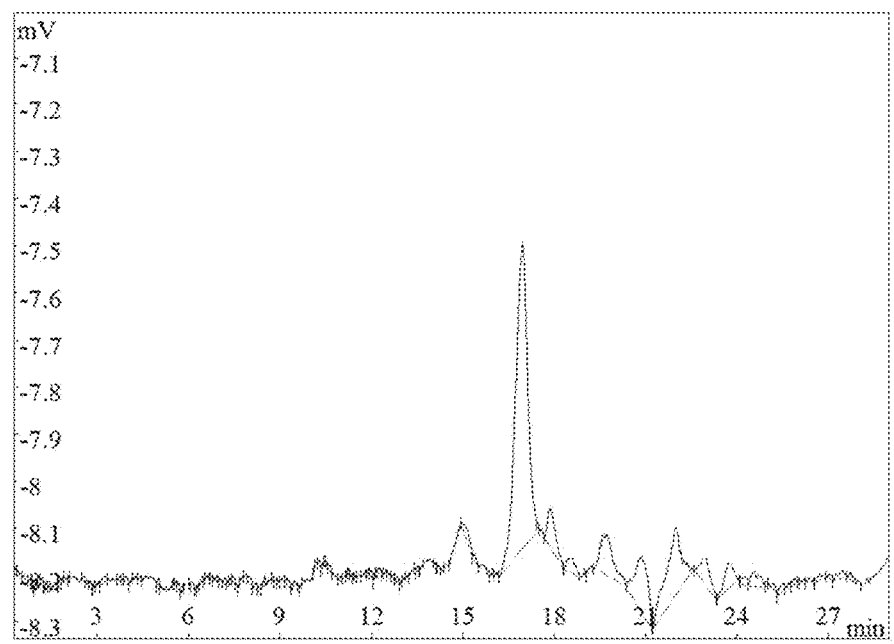

FIGS. 5A-5C show the chromatograms of the conjugate (GDox) in serum and in buffer (FIGS. 5A and 5B), as well as a control serum without conjugate (FIG. 5C). The peak at 17 minutes in the serum sample (FIG. 5B) is not from the conjugate. This peak is from a serum protein with visible absorbance at the 488 nm wavelength of detection as evidenced by its presence in the serum without the conjugate but its absence in the buffer control with the conjugate.

Figure 5D:
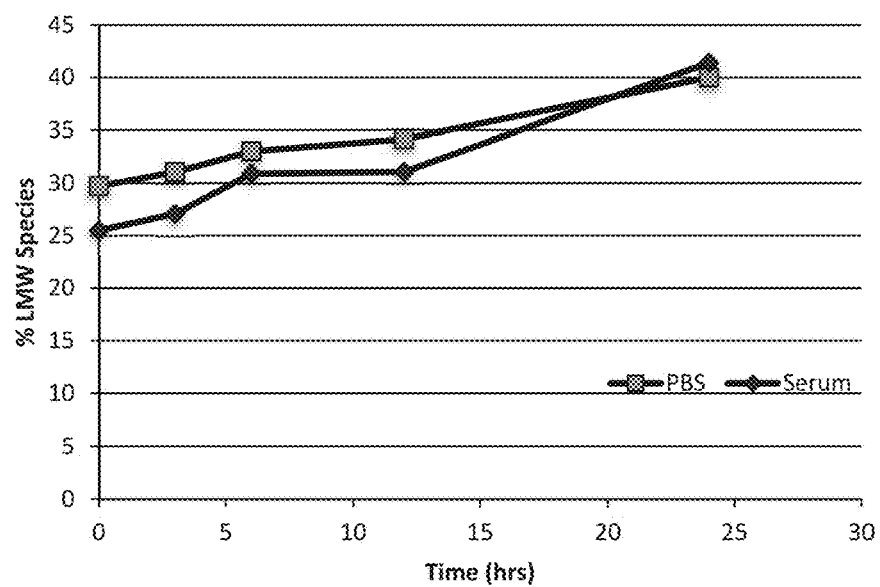

Overall, the chromatograms show little change in the molecular distribution for 12 hrs and up to 24 hr. A small drop in the alpha chain of 100 kD (15 min) is observed but the overall degradation in serum is relatively small as shown in the graph of % LMW with time (FIG. 5D). The graph illustrates the small extent of degradation in serum up to 24 hours based on the change from the initial % LMW value of 26% to the final value of 41%. A similar change is shown by the conjugate in buffer.

Discussion

The small increase of low molecular weight species over 24 hrs as a measure of degradation is essentially the same for the control buffer and serum. This result shows that the general enzymes in the serum do not degrade GDox and that the small degradation observed in serum can be attributed to the same causes in the buffer, i.e., pH and temperature. Thus, the conjugate can be expected to maintain a high molecular weight in the blood circulation which then can allow tumor accumulation of GDox from the EPR effect. Such tumor accumulation is also expected to produce a substantial anti-tumor effect with minimal toxic system side effects compared to the free drug.

What is claimed is:

1. A high molecular weight compound comprising gelatin and doxorubicin, wherein the gelatin is covalently linked to doxorubicin through a cleavable linker, and wherein the average molecular weight of the compound is at least 40 kDa.

2. The compound of claim 1, wherein the cleavable linker comprises a cleavable portion selected from a group consisting of: a pH-sensitive portion, a heat-sensitive portion, a light-sensitive portion, an enzymatically-cleavable portion, and a combination thereof.

3. The compound of claim 2, wherein the pH-sensitive portion comprises a hydrazone bond, an ester, —S—S—, a carbamate, a vinyl ether, a silyl ether, or a combination thereof.

4. The compound of claim 1, wherein the cleavable linker further comprises a spacer.

5. The compound of claim 1, wherein the linker comprises a hydrazine bond and glycylglycine.

6. The compound of claim 1, corresponding to Formula (I):

Formula I

<chemical structure> wherein x is determined by the molecular weight of the compound.

7. A method of preparing a compound comprising gelatin and doxorubicin, the method comprising reacting a gelatin-linker conjugate with doxorubicin in formamide, wherein the gelatin-linker conjugate is reacted with the doxorubicin in pH less than 7.

8. The method of claim 7, further comprising:
 (i) reacting gelatin dissolved in formamide with a linker to form the gelatin-linker conjugate; and
 (ii) precipitating the gelatin-linker conjugate with an alcohol.

9. The method of claim 8, wherein the linker is cleavable.

10. The method of claim 9, wherein the linker comprises a cleavable portion selected from a group consisting of: a pH-sensitive portion, a heat-sensitive portion, a light-sensitive portion, an enzymatically-cleavable portion, and a combination thereof.

11. The method of claim 10, wherein the linker comprises a hydrazine bond.

12. The method of claim 7, wherein the gelatin-linker conjugate is a gelatin-glycylglycine-hydrazide conjugate.

13. The method of claim 12, further comprising:
 (i) reacting gelatin dissolved in formamide with glycylglycine to form a gelatin glycylglycine conjugate;
 (ii) precipitating the gelatin-glycylglycine conjugate with a first alcohol;
 (iii) reacting the gelatin-glycylglycine conjugate with hydrazine in formamide to form the gelatin-glycylglycine-hydrazide conjugate; and
 (iv) precipitating the gelatin-glycylglycine-hydrazide conjugate with a second alcohol.

14. The method of claim 13, further comprising adding 1-ethyl-3-(3-dimethylaminopropyl)carbodiimide (EDC) in step (i) or further comprising adding EDC in step (iii).

15. The method of claim 13, wherein glycylglycine is attached to a solid support in step (i).

16. The method of claim 12, wherein the gelatin-glycylglycine-hydrazide conjugate is reacted with doxorubicin in pH less than 7 and in the presence of a drying agent.

17. A method of preparing a compound comprising gelatin and doxorubicin, the method comprising reacting an amino-blocked doxorubicin-hydrazide-glycylglycine conjugate with high molecular weight gelatin in formamide in pH of less than 7.

18. The method of claim 17, further comprising;
 (i) reacting doxorubicin with an amine to form an amino-blocked doxorubicin;
 (ii) reacting the amino-blocked doxorubicin with hydrazine to form an amino-blocked doxorubicin-hydrazide conjugate; and
 (iii) reacting the amino-blocked doxorubicin-hydrazide conjugate with glycylglycine to form the amino-blocked doxorubicin-hydrazide-glycylglycine conjugate.

19. A method of treating cancer in a subject, the method comprising administering a pharmaceutically-effective amount of a compound of claim 1 to the subject.

20. The method of claim 19, wherein the administering is local or systemic.

21. A pharmaceutical composition comprising a compound of claim 1 and a pharmaceutically acceptable carrier.

* * * * *